(12) United States Patent
Lin et al.

(10) Patent No.: US 7,109,220 B2
(45) Date of Patent: Sep. 19, 2006

(54) AMINO SUBSTITUTED PYRIDINYL METHANONE COMPOUNDS USEFUL IN TREATING KINASE DISORDERS

(75) Inventors: Ronghui Lin, East Brunswick, NJ (US); Steven K. Wetter, Flemington, NJ (US); Yanhua Lu, Green Brook, NJ (US); Peter J. Connolly, New Providence, NJ (US); Stuart Emanuel, Doylestown, PA (US); Robert H. Gruninger, Easton, PA (US); Steven A. Middleton, Flemington, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 10/981,087

(22) Filed: Nov. 4, 2004

(65) Prior Publication Data

US 2005/0124610 A1     Jun. 9, 2005

Related U.S. Application Data

(60) Provisional application No. 60/523,478, filed on Nov. 19, 2003.

(51) Int. Cl.
*A61K 31/44* (2006.01)
*C07D 213/60* (2006.01)

(52) U.S. Cl. .................. 514/349; 546/297; 546/255; 546/262; 546/280.4; 546/283.4; 546/290; 546/307; 514/332; 514/336; 514/352

(58) Field of Classification Search ............... 514/349, 514/332, 336, 352; 546/297, 308, 307, 290, 546/283.4, 280.4, 262, 255
See application file for complete search history.

(56) References Cited

U.S. PATENT DOCUMENTS 3,946,024 A * 3/1976 Fleckenstein et al. ....... 546/288
3,980,659 A   9/1976 Fleckenstein et al.

OTHER PUBLICATIONS

PCT Search Report, PCT/US04/36880, Feb. 9, 2005.

* cited by examiner

*Primary Examiner*—Charanjit S. Aulakh

(57) ABSTRACT

The present invention provides amino substituted pyridinyl methanone compounds; pharmaceutical compositions comprising the compounds and methods of synthesis thereof. The compounds, which are cyclin dependent kinase (CDK) inhibitors, can be used to treat or ameliorate CDK mediated disorders. The invention thus also provides the therapeutic or prophylactic use of the compounds and/or pharmaceutical compositions to treat such disorders.

10 Claims, No Drawings

AMINO SUBSTITUTED PYRIDINYL METHANONE COMPOUNDS USEFUL IN TREATING KINASE DISORDERS

CROSS REFERENCE TO RELATED APPLICATIONS

This application claims priority to Application No. 60/523,478 filed on Nov. 19, 2003.

FIELD OF THE INVENTION

The present invention relates to a series of amino substituted pyridinyl methanone compounds, pharmaceutical compositions and methods for use thereof. More particularly, the amino substituted pyridinyl methanone compounds of the present invention are cyclin dependent kinase (CDK) inhibitors useful in treating or ameliorating a CDK mediated disorder.

BACKGROUND OF THE INVENTION

Uncontrolled cell proliferation is the insignia of cancer. Cell proliferation in response to various stimuli is manifested by a deregulation of the cell division cycle, the process by which cells multiply and divide. Tumor cells typically have damage to the genes that directly or indirectly regulate progression through the cell division cycle.

CDKs constitute a class of enzymes that play critical roles in regulating the transitions between different phases of the cell cycle, such as the progression from a quiescent stage in $G_1$ (the gap between mitosis and the onset of DNA replication for a new round of cell division) to S (the period of DNA synthesis), or the progression from $G_2$ to M phase, in which active mitosis and cell-division occur. See, e.g., the articles compiled in *Science*, vol. 274 (1996), p. 1643–1677; and *Ann. Rev. Cell Dev. Biol*, vol. 13 (1997), pp. 261–291. CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, the CDKs display an absolute dependence on the cyclin subunit in order to phosphorylate their target substrates, and different kinase/cyclin pairs function to regulate progression through specific portions of the cell cycle.

The D cyclins are sensitive to extracellular growth signals and become activated in response to mitogens during the $G_1$ phase of the cell cycle. CDK4/cyclin D plays an important role in cell cycle progression by phosporylating, and thereby inactivating, the retinoblastoma protein (Rb). Hypophosphorylated Rb binds to a family of transcriptional regulators, but upon hyperphosphorylation of Rb by CDK4/cyclin D, these transcription factors are released to activate genes whose products are responsible for S phase progression. Rb phosphorylation and inactivation by CDK4/cyclin D permit passage of the cell beyond the restriction point of the $G_1$ phase, whereupon sensitivity to extracellular growth or inhibitory signals is lost and the cell is committed to cell division. During late $G_1$, Rb is also phosphorylated and inactivated by CDK2/cyclin E, and recent evidence indicates that CDK2/cyclin E can also regulate progression into S phase through a parallel pathway that is independent of Rb phosphorylation (see Lukas et al., "Cyclin E-induced S Phase Without Activation of the pRb/E2F Pathway," *Genes and Dev.*, vol. 11 (1997), pp. 1479–1492).

The progression from $G_1$ to S phase, accomplished by the action of CDK4/cyclin D and CDK2/cyclin E, is subject to a variety of growth regulatory mechanisms, both negative and positive. Growth stimuli, such as mitogens, caused increased synthesis of cyclin D1 and thus increased functional CDK4. By contrast, cell growth can be "reined in," in response to DNA damage or negative growth stimuli, by the induction of endogenous inhibitory proteins. These naturally occurring protein inhibitors include $p21^{WAF1/CIP1}$, $p27^{KIP1}$, and the $p16^{NK4}$ family, the latter of which inhibit CDK4 exclusively (see Harper, "Cyclin Dependent Kinase Inhibitors," *Cancer Surv.*, vol. 29 (1997), pp. 91–107). Aberrations in this control system, particularly those that affect the function of CDK4 and CKD2, are implicated in the advancement of cells to the highly proliferative state characteristic of malignancies, such as familial melanomas, esophageal carcinomas, and pancreatic cancers (see, e.g., Hall and Peters, "Genetic Alterations of Cyclins, Cyclin-Dependent Kinases, and CDK Inhibitors in Human Cancer," *Adv. Cancer Res.*, vol. 68 (1996), pp. 67–108; and Kamb et al., "A Cell Cycle Regulator Potentially Involved in Genesis of Many Tumor Types," *Science*, vol. 264 (1994), pp. 436–440). Overexpression of cyclin D1 is linked to esophageal, breast, and squamous cell carcinomas (see, e.g., DelSal et al., "Cell Cycle and Cancer: Critical Events at the $G_1$ Restriction Point," *Critical Rev. Oncogenesis*, vol. 71 (1996), pp. 127–142). Genes encoding the CDK4-specific inhibitors of the p16 family frequently have deletions and mutations in familial melanoma, gliomas, leukemias, sarcomas, and pancreatic, non-small cell lung, and head and neck carcinomas (see Nobori et al., "Deletions of the Cyclin-Dependent Kinase-4 Inhibitor Gene in Multiple Human Cancers," *Nature*, vol. 368 (1994), pp. 753–756). Amplification and/or overexpression of cyclin E has also been observed in a wide variety of solid tumors, and elevated cyclin E levels have been correlated with poor prognosis. In addition, the cellular levels of the CDK inhibitor p27, which acts as both a substrate and inhibitor of CDK2/cyclin E, are abnormally low in breast, colon, and prostate cancers, and the expression levels of p27 are inversely correlated with the state of disease (see Loda et al., "Increased Proteasome-dependent Degradation of the Cyclin-Dependent Kinase Inhibitor p27 in Aggressive Colorectal Carcinomas," *Nature Medicine*, vol. 3 (1997), pp. 231–234). The p21 protein also appear to transmit the p53 tumor-suppression signal to the CDKs; thus, the mutation of p53 in approximately 50% of all human cancers may indirectly result in deregulation of CDK activity.

There is a need, for small-molecule compounds that may be readily synthesized and are potent inhibitors of one or more CDKs or CDK/cyclin complexes.

SUMMARY OF THE INVENTION

Accordingly, one object of the invention is to attain compounds and drug compositions that inhibit the activity of one or more CDKs or cyclin complexes thereof. A further object is to provide an effective method of treating cancer indications through CDK inhibition. Another object is to achieve pharmaceutical compositions containing compounds effective to block the transition of cancer cells into their proliferative phase. These and other objects and advantages of the invention, which will become apparent in light of the detailed description below, are achieved through use of the compounds of the invention described below.

The present invention provides amino substituted pyridinyl methanone compounds of Formula (I):

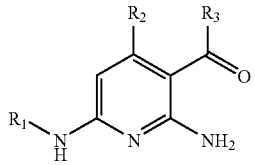

Formula (I)

and pharmaceutically acceptable forms thereof,
wherein
$R_1$ is selected from:
(1) hydrogen;
(2) aryl optionally substituted with
  (a) one or more substituents independently selected from $C_{1-8}$alkyl, $C_{1-8}$alkoxy, amino (optionally mono or disubstituted with $C_{1-8}$alkyl), cyano, halogen, halogen-substituted $C_{1-8}$alkyl, halogen-substituted $C_{1-8}$alkoxy, hydroxy or nitro;
  (b) one —$SO_2$-amino substituent optionally mono or disubstituted on amino with $C_{1-8}$alkyl, $C_{1-8}$alkylamino (optionally mono or disubstituted on amino with $C_{1-8}$alkyl), $C_{1-8}$alkyl-aryl, C(O)O-t-butyl or heteroaryl;
  (c) one —$SO_2$-heterocyclyl substituent;
  (d) one —$NHSO_2$-aryl substituent;
  (e) one —C(O)amino substituent optionally mono or disubstituted on amino with $C_{1-8}$alkyl;
  (f) one —NHC(O)— substituent terminating with $C_{1-8}$alkyl or aryl;
  (g) one —$CO_2$— substituent terminating with hydrogen or $C_{1-8}$alkyl;
  (h) one —NHC(O)NH-aryl substituent; or,
  (i) one —NHC(S)NH-aryl substituent;
  (j) one substituent selected from heterocyclyl, aryl or heteroaryl;
(3) heteroaryl optionally substituted with one or more substituents independently selected from $C_{1-8}$alkyl, $C_{1-8}$alkoxy, amino (optionally mono or disubstituted with $C_{1-8}$alkyl), cyano, halogen, halogen-substituted $C_{1-8}$alkyl, halogen-substituted $C_{1-8}$alkoxy, hydroxy or nitro;
(4) —C(O)— terminating with aryl, heteroaryl or alkyl;
(5) —C(O)NH— substituent terminating with aryl, heteroaryl or alkyl; or,
(6) —C(S)NH— substituent terminating with aryl, heteroaryl or alkyl;
$R_2$ is selected from hydrogen, $C_{1-8}$alkyl, $C_{1-8}$alkoxy, amino (optionally mono or disubstituted with $C_{1-8}$alkyl), cyano, halogen, hydroxy, mercapto, S($C_{1-8}$)alkyl or nitro;
wherein $C_{1-8}$alkyl and $C_{1-8}$alkoxy, whether alone or as part of a substituent group are optionally substituted with one or more substituents independently selected from halogen or amino (optionally mono or disubstituted on amino with $C_{1-8}$alkyl);
$R_3$ is selected from aryl or heteroaryl,
(1) wherein aryl is optionally substituted with one or more substituents independently selected from $C_{1-8}$alkyl, $C_{1-8}$alkoxy, amino (optionally mono or disubstituted with $C_{1-8}$alkyl), cyano, halogen, halogen-substituted $C_{1-8}$alkyl, halogen-substituted $C_{1-8}$alkoxy, hydroxy or nitro; and
(2) wherein heteroaryl is optionally substituted on
  (a) a ring carbon atom with one or more substituents selected from $C_{1-8}$alkyl, $C_{1-8}$alkoxy, amino (optionally mono or disubstituted with $C_{1-8}$alkyl), cyano, halogen, halogen-substituted $C_{1-8}$alkyl, halogen-substituted $C_{1-8}$alkoxy, hydroxy or nitro; or on
  (b) a ring nitrogen atom with one $C_{1-8}$alkyl substituent.

An embodiment of the present invention includes an amino substituted pyridinyl methanone compound of Formula (I) wherein the compound is a CDK inhibitor.

An embodiment of the present invention includes a method for using the amino substituted pyridinyl methanone compounds of Formula (I) in treating or ameliorating a CDK mediated disorder.

DETAILED DESCRIPTION OF THE INVENTION

Embodiments of the present invention include compounds of Formula (I) wherein $R_1$ is hydrogen.

Embodiments of the present invention include compounds of Formula (I) wherein $R_1$ is phenyl optionally substituted with
  (a) one or more substituents independently selected from $C_{1-8}$alkyl, $C_{1-8}$alkoxy, amino (optionally mono or disubstituted with $C_{1-8}$alkyl), cyano, halogen, halogen-substituted $C_{1-8}$alkyl, halogen-substituted $C_{1-8}$alkoxy, hydroxy or nitro;
  (b) one —$SO_2$-amino substituent optionally mono or disubstituted on amino with $C_{1-8}$alkyl, $C_{1-8}$alkylamino (optionally mono or disubstituted on amino with $C_{1-8}$alkyl), $C_{1-8}$alkyl-aryl, C(O)O-t-butyl or heteroaryl;
  (c) one —$SO_2$-heterocyclyl substituent;
  (d) one —$NHSO_2$-aryl substituent;
  (e) one —C(O)amino substituent optionally mono or disubstituted on amino with $C_{1-8}$alkyl;
  (f) one —NHC(O)— substituent terminating with $C_{1-8}$alkyl or aryl;
  (g) one —$CO_2$— substituent terminating with hydrogen or $C_{1-8}$alkyl;
  (h) one —NHC(O)NH-aryl substituent;
  (i) one —NHC(S)NH-aryl substituent; or,
  (j) one substituent selected from heterocyclyl, aryl or heteroaryl.

Embodiments of the present invention include compounds of Formula (I) wherein $R_1$ is phenyl optionally substituted with
  (a) one or more substituents independently selected from $C_{1-8}$alkyl, $C_{1-8}$alkoxy, amino (optionally mono or disubstituted with $C_{1-8}$alkyl), cyano, halogen, halogen-substituted $C_{1-8}$alkyl, halogen-substituted $C_{1-8}$alkoxy, hydroxy or nitro;
  (b) one —$SO_2$-amino substituent optionally mono or disubstituted on amino with $C_{1-8}$alkyl, $C_{1-8}$alkylamino (optionally mono or disubstituted on amino with $C_{1-8}$alkyl), $C_{1-8}$alkyl-aryl, C(O)O-t-butyl or heteroaryl;
  (c) one —$SO_2$-heterocyclyl substituent;
  (d) one —$NHSO_2$-phenyl substituent;
  (e) one —C(O)amino substituent optionally mono or disubstituted on amino with $C_{1-8}$alkyl;
  (f) one —NHC(O)— substituent terminating with $C_{1-8}$alkyl or phenyl;
  (g) one —$CO_2$— substituent terminating with hydrogen or $C_{1-8}$alkyl;
  (h) one —NHC(O)NH-phenyl substituent;
  (i) one —NHC(S)NH-phenyl substituent; or,
  (j) one substituent selected from heterocyclyl, phenyl or heteroaryl.

Embodiments of the present invention include compounds of Formula (I) wherein $R_1$ is phenyl optionally substituted with
- (a) one or more substituents independently selected from amino, (optionally mono or disubstituted with $C_{1-8}$alkyl), cyano, halogen or nitro;
- (b) one —$SO_2$-amino substituent optionally mono or disubstituted on amino with $C_{1-8}$alkyl, $C_{1-8}$alkylamino (optionally mono or disubstituted on amino with $C_{1-8}$alkyl), $C_{1-8}$alkyl-aryl, C(O)O-t-butyl or heteroaryl;
- (c) one —$SO_2$-heterocyclyl substituent;
- (d) one —$NHSO_2$-phenyl substituent;
- (e) one —C(O)amino substituent;
- (f) one —NHC(O)— substituent terminating with $C_{1-8}$alkyl or phenyl;
- (g) one —$CO_2$— substituent terminating with hydrogen or $C_{1-8}$alkyl;
- (h) one —NHC(O)NH-phenyl substituent; or,
- (i) one —NHC(S)NH-phenyl substituent.

Embodiments of the present invention include compounds of Formula (I) wherein $R_1$ is heterocyclyl, whether alone or as part of a substituent group, wherein heterocyclyl is selected from piperidinyl, piperazinyl, morpholinyl, thiomorpholinyl or tetrahydro-pyridazinyl.

Embodiments of the present invention include compounds of Formula (I) wherein $R_1$ is heteroaryl optionally substituted with one or more substituents independently selected from $C_{1-4}$alkyl, $C_{1-4}$alkoxy, amino (optionally mono or disubstituted with $C_{1-4}$alkyl), cyano, halogen, halogen-substituted $C_{1-4}$alkyl, halogen-substituted $C_{1-4}$alkoxy, hydroxy or nitro.

Embodiments of the present invention include compounds of Formula (I) wherein $R_1$ is heteroaryl, whether alone or as part of a substituent group, wherein heteroaryl is selected from pyrrolyl, oxazolyl, thiazolyl, imidazolyl, pyrazolyl, isoxazolyl, isothiazolyl or pyridinyl.

Embodiments of the present invention include compounds of Formula (I) wherein $R_1$ is pyridinyl.

Embodiments of the present invention include compounds of Formula (I) wherein $R_1$ is —C(O)-aryl.

Embodiments of the present invention include compounds of Formula (I) wherein $R_1$ is —C(O)-phenyl.

Embodiments of the present invention include compounds of Formula (I) wherein $R_1$ is —C(O)NH-aryl.

Embodiments of the present invention include compounds of Formula (I) wherein $R_1$ is —C(O)NH-phenyl.

Embodiments of the present invention include compounds of Formula (I) wherein $R_1$ is —C(S)NH-aryl.

Embodiments of the present invention include compounds of Formula (I) wherein $R_1$ is —C(S)NH-phenyl.

Embodiments of the present invention include compounds of Formula (I) wherein $R_2$ is selected from hydrogen, $C_{1-4}$alkyl, $C_{1-4}$alkoxy, amino (optionally mono or disubstituted with $C_{1-4}$alkyl), cyano, halogen, hydroxy, mercapto, $S(C_{1-4})$alkyl or nitro; wherein $C_{1-4}$alkyl and $C_{1-4}$alkoxy, whether alone or as part of a substituent group are optionally substituted with one or more substituents independently selected from halogen or amino (optionally mono or disubstituted on amino with $C_{1-4}$alkyl).

Embodiments of the present invention include compounds of Formula (I) wherein $R_2$ is selected from hydrogen, $C_{1-4}$alkoxy or amino (optionally mono or disubstituted with $C_{1-4}$alkyl), wherein $C_{1-4}$alkoxy is optionally substituted with one or more substituents independently selected from halogen or amino (optionally mono or disubstituted on amino with $C_{1-4}$alkyl).

Embodiments of the present invention include compounds of Formula (I) wherein $R_2$ is selected from hydrogen or $C_{1-4}$alkoxy.

Embodiments of the present invention include compounds of Formula (I) wherein $R_3$ is aryl optionally substituted with one or more substituents independently selected from $C_{1-8}$alkyl, $C_{1-8}$alkoxy, amino (optionally mono or disubstituted with $C_{1-4}$alkyl), cyano, halogen, halogen-substituted $C_{1-8}$alkyl, halogen-substituted $C_{1-8}$alkoxy, hydroxy or nitro.

Embodiments of the present invention include compounds of Formula (I) wherein $R_3$ is phenyl optionally substituted with one or more substituents independently selected from $C_{1-8}$alkyl, $C_{1-8}$alkoxy, amino (optionally mono or disubstituted with $C_{1-4}$alkyl), cyano, halogen, halogen-substituted $C_{1-8}$alkyl, halogen-substituted $C_{1-8}$alkoxy, hydroxy or nitro.

Embodiments of the present invention include compounds of Formula (I) wherein $R_3$ is phenyl optionally substituted with one or more halogen substituents.

Embodiments of the present invention include compounds of Formula (I) wherein $R_3$ is heteroaryl.

Embodiments of the present invention include compounds of Formula (I) wherein $R_3$ is selected from thienyl or furyl.

Embodiments of the present invention include compounds of Formula (I) wherein the compound of Formula (I) is selected from a compound of Formula (Ia), wherein $R_2$ is hydrogen and $R_1$ and $R_3$ are dependently selected from:

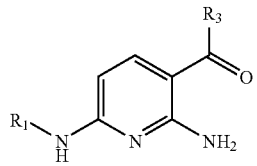

Formula (Ia)

| Cpd | $R_1$ | $R_3$ |
|---|---|---|
| 1 | H | (2,6-$F_2$)Ph |
| 2 | H | (2-F)Ph |
| 2b | [4-$SO_2N(CH_2$—Ph$)_2$]Ph | (2,6-$F_2$)Ph |
| 3 | H | Ph |
| 4 | H | fur-2-yl |
| 5 | H | thien-2-yl |
| 6 | (4-$SO_2NH_2$)Ph | (2,6-$F_2$)Ph |
| 7 | [4-$SO_2N(CH_3)_2$]Ph | (2,6-$F_2$)Ph |
| 8 | (4-CN)Ph | (2,6-$F_2$)Ph |
| 9 | (4-$NO_2$)Ph | (2,6-$F_2$)Ph |
| 10 | (3-$NO_2$)Ph | (2,6-$F_2$)Ph |
| 11 | (3-Cl)Ph | (2,6-$F_2$)Ph |
| 12 | (2-$NO_2$)Ph | (2,6-$F_2$)Ph |
| 13 | Ph | (2,6-$F_2$)Ph |
| 14 | pyridin-2-yl | (2,6-$F_2$)Ph |
| 15 | [4-C(O)$NH_2$]Ph | (2,6-$F_2$)Ph |
| 16 | (4-$CO_2$H)Ph | (2,6-$F_2$)Ph |
| 17 | (4-$NH_2$)Ph | (2,6-$F_2$)Ph |
| 18 | [4-NH(CH$_3$)]Ph | (2,6-$F_2$)Ph |
| 19 | [4-$SO_2$NH(Ph)]Ph | (2,6-$F_2$)Ph |
| 20 | [2-$NH_2$]Ph | (2,6-$F_2$)Ph |
| 21 | [2-NHC(O)CH$_3$]Ph | (2,6-$F_2$)Ph |
| 22 | [2-NHC(O)Ph]Ph | (2,6-$F_2$)Ph |
| 23 | (2-NHSO$_2$Ph)Ph | (2,6-$F_2$)Ph |
| 24 | [4-$SO_2N(CH_3)_2$]Ph | (2-F)Ph |
| 25 | [4-$SO_2N(CH_3)_2$]Ph | Ph |
| 26 | [4-$SO_2N(CH_2CH_3)_2$]Ph | Ph |

-continued

Formula (Ia)

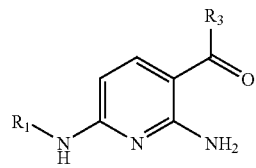

| Cpd | R₁ | R₃ |
|---|---|---|
| 27 | [4-SO₂N(CH₃)₂]Ph | fur-2-yl |
| 28 | [4-SO₂N(CH₂CH₃)₂]Ph | fur-2-yl, and |
| 29 | [4-SO₂N(CH₃)₂]Ph | thien-2-yl. |

Embodiments of the present invention include compounds of Formula (I) wherein the compound of Formula (I) is selected from a compound of Formula (Ib), wherein R₂ is n-butoxy, R₃ is (2,6-F₂)Ph and R₁ is selected from:

Formula (Ib)

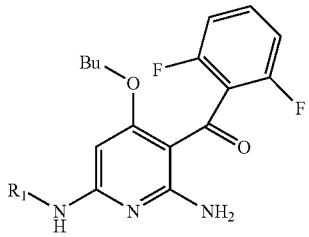

| Cpd | R₁ |
|---|---|
| 31 | H |
| 32 | C(O)NH(Ph) |
| 33 | C(S)NH(Ph) |
| 34 | C(O)Ph |
| 35 | [4-SO₂N(CH₃)₂]Ph |
| 36 | (4-SO₂NH₂)Ph |

Embodiments of the present invention include compounds selected from:

Cpd 1

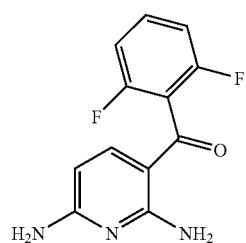

Cpd 2

Cpd 2b

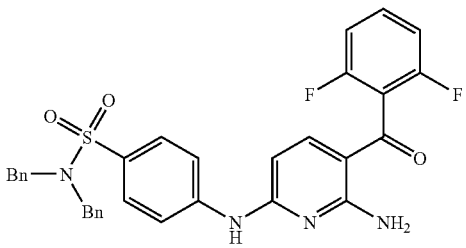

Cpd 3

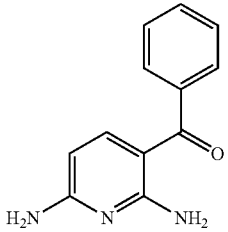

Cpd 4

Cpd 5

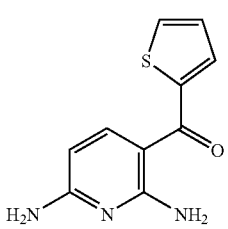

Cpd 6

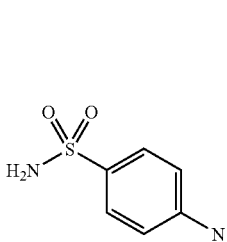

Cpd 7

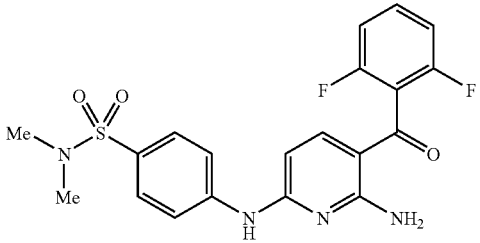

-continued
Cpd 8
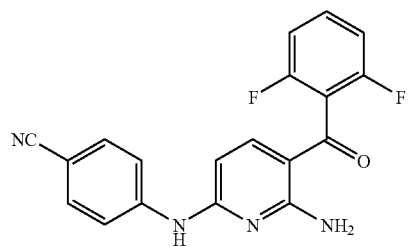
Cpd 9
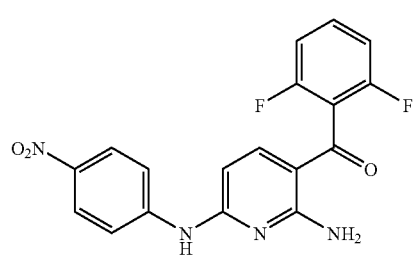
Cpd 10
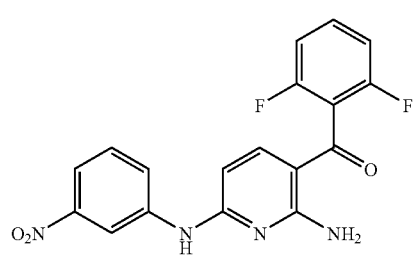
Cpd 11
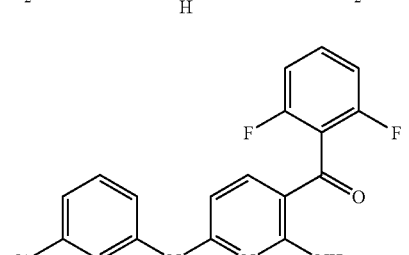
Cpd 12
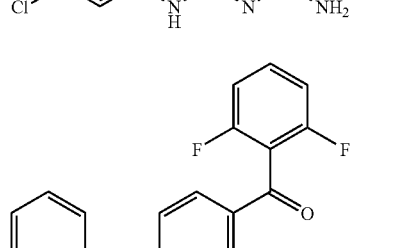
Cpd 13
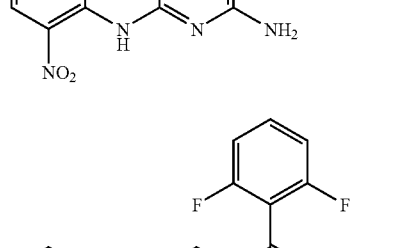
-continued
Cpd 14
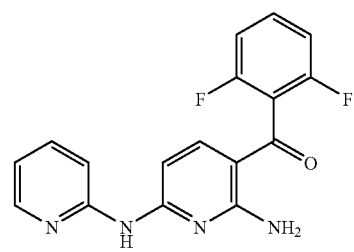
Cpd 15
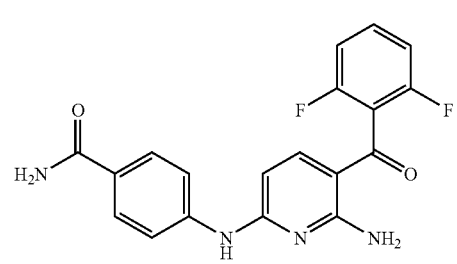
Cpd 16
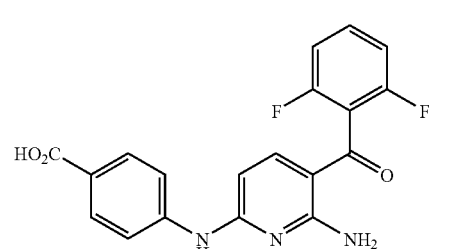
Cpd 17
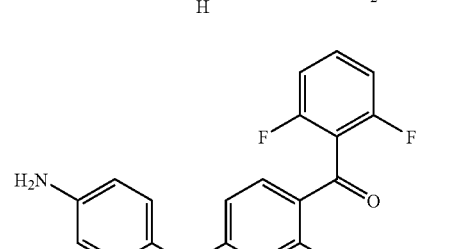
Cpd 18
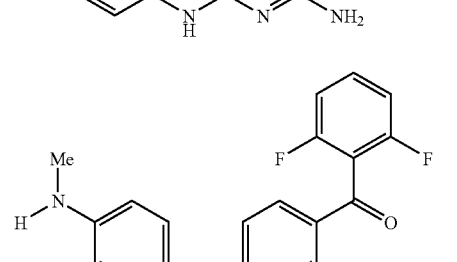
Cpd 19
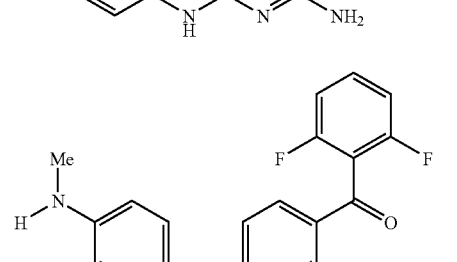

-continued
Cpd 20
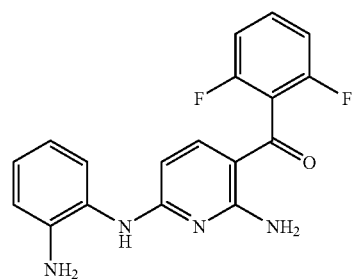
Cpd 21
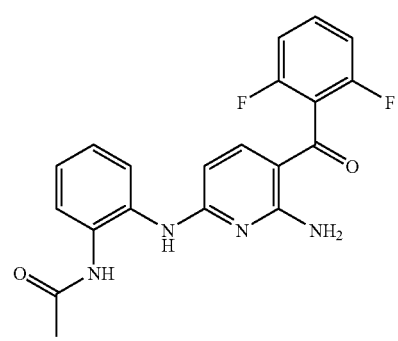
Cpd 22
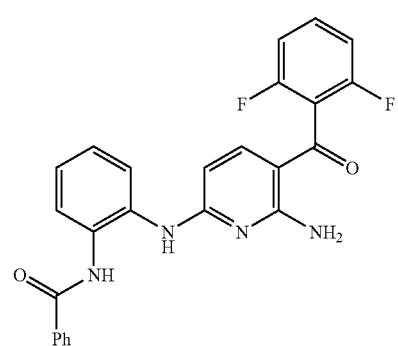
Cpd 23
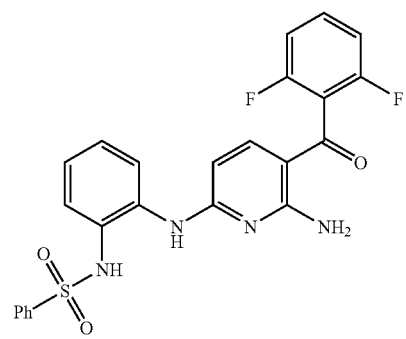
Cpd 24
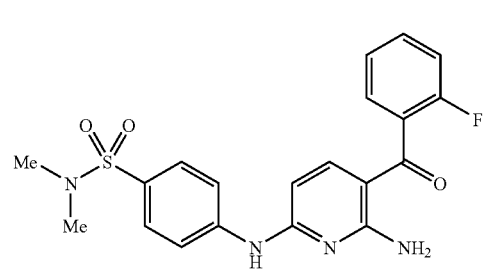
-continued
Cpd 25
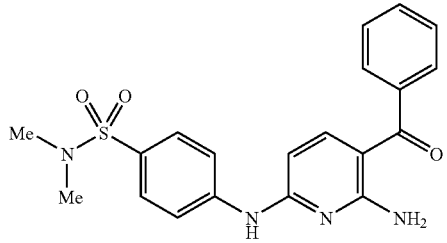
Cpd 26
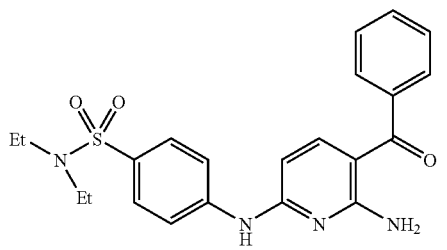
Cpd 27
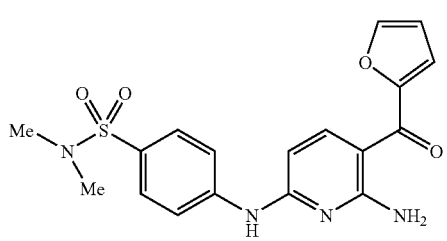
Cpd 28
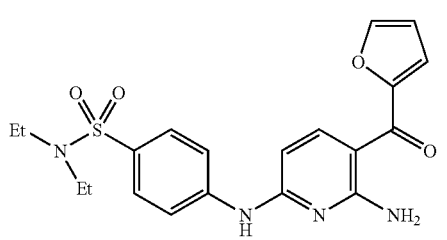
Cpd 29
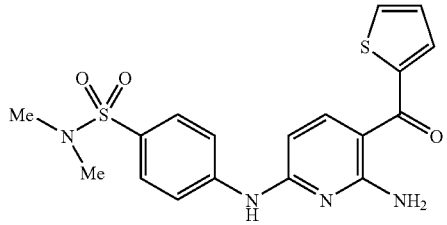
Cpd 31
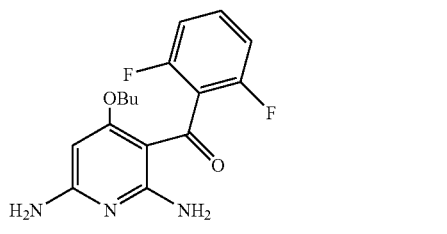

-continued

Cpd 32
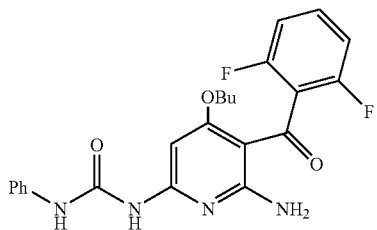

Cpd 33
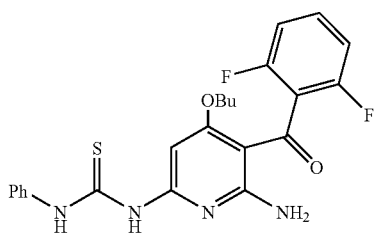

Cpd 34
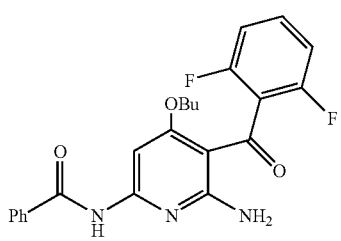

Cpd 35
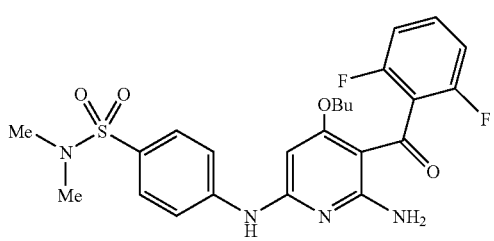

Cpd 36
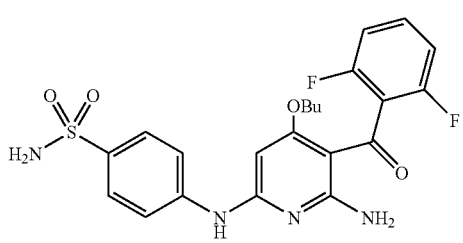

Chemical Definitions & Nomenclature

As used herein, the following terms are intended to have the following meanings (additional definitions are provided throughout the Specification):

The term "$C_{a-b}$" (where a and b are integers referring to a designated number of carbon atoms) refers to an alkyl or to the alkyl portion of a radical in which alkyl appears as the prefix root containing from a to b carbon atoms inclusive. For example, $C_{1-4}$ denotes a radical containing 1, 2, 3 or 4 carbon atoms.

The term "alkyl," whether used alone or as part of a substituent group, refers to a saturated branched or straight chain monovalent hydrocarbon radical, wherein the radical is derived by the removal of one hydrogen atom from a single carbon atom. Typical alkyl radicals include, but are not limited to, methyl, ethyl, propyl, butyl and the like. Embodiments include, e.g., the alkyl groups $C_{1-8}$alkyl or $C_{1-4}$alkyl.

The term "alkoxy" refers to a saturated or partially unsaturated branched or straight chain monovalent hydrocarbon alcohol radical derived by the removal of the hydrogen atom from the hydroxide oxygen substituent on an alcohol parent alkyl radical. Embodiments include, e.g., the alkoxy groups $C_{1-8}$alkoxy or $C_{1-4}$alkoxy.

The term "heterocyclyl" refers to a saturated or partially unsaturated monocyclic ring radical of from 5 to 10 ring members derived by the removal of one hydrogen atom from a single ring carbon atom and in which one or more ring atoms are a heteroatom selected from N, P, O or S. Embodiments include rings wherein 1, 2, 3 or 4 members of the ring are a nitrogen atom, or 0, 1, 2 or 3 members of the ring are nitrogen atoms and 1 member is an oxygen or sulfur atom. Typical heterocyclyl radicals include, and are not limited to, dihydro-1H-pyrrole (including 2-pyrrolinyl or 3-pyrrolinyl), pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furyl, tetrahydro-thienyl, tetrahydro-pyranyl, tetrahydro-pyridazinyl and the like.

The term "aryl" refers to an aromatic cyclic hydrocarbon ring radical derived by the removal of one hydrogen atom from a single carbon atom of a parent aromatic ring system. Typical aryl radicals include, and are not limited to, phenyl, naphthalenyl, fluorenyl, indenyl, azulenyl, anthracenyl and the like.

The term "parent aromatic ring system" refers to an unsaturated or partially saturated monocyclic ring of 6 carbon atom members or unsaturated or partially saturated polycyclic, fused ring systems of from 10 to 20 carbon atom members having an "aromatic" conjugated π electron system. Specifically included within the definition of "parent aromatic ring system" are fused ring systems in which one or more rings are aromatic and one or more rings are unsaturated or partially saturated.

The term "heteroaryl" refers to a heteroaromatic hydrocarbon ring radical derived by the removal of one hydrogen atom from a single ring carbon atom of a parent heteroaromatic ring system and in which one or more ring carbon atoms are independently replaced with a heteroatom selected from N, P, O or S. Typical heteroaryl radicals include, and are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolizinyl, indolyl, isoindolyl, benzo[b]furyl, benzo[b]thienyl, indazolyl, benzimidazolyl, benzthiazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like.

The term "parent heteroaromatic ring system" refers to an unsaturated or partially saturated monocyclic ring of 5 or 6 ring members wherein the ring members consist of carbon atoms and at least one heteroatom selected from N, P, O or S or unsaturated or partially saturated polycyclic, fused ring systems of from 5 to 20 ring members wherein the ring members consist of carbon atoms and at least one heteroatom selected from N, P, O or S. Embodiments include rings wherein 1, 2, 3 or 4 members of the ring are a nitrogen atom, or 0, 1, 2 or 3 members of the ring are nitrogen atoms and 1 member is an oxygen or sulfur atom. In other embodiments where allowed, up to two adjacent ring members are heteroatoms. Specifically included within the definition of "parent heteroaromatic ring system" are fused ring systems in which one or more rings are aromatic and one or more rings are saturated or unsaturated wherein one or more carbon atoms are each independently replaced with a heteroatom.

Where a radical is "substituted," the term "substituted" refers to the independent replacement of one or more hydrogen atoms within the radical with that amount of substitutents allowed by available valences. The term "independent(ly)" means that when a group or radical is substituted with more than one substituent that the substituents may be the same or different. Substitution is not limited to a terminal atom, but may occur either within the radical or on a terminal atom. The term "dependently substituted" means that the subsituents are specified in an indicated combination of structure variables. Where a radical or group of radicals is refered to as being "optionally present," the term "optionally present" refers to the replacement of one or more hydrogen atoms at a point of attachment on a core structure with that amount of radicals allowed by available valences; wherein, the point of attachment is otherwise saturated or aromatic when the radical(s) is (are) not present.

In general, IUPAC nomenclature rules are used throughout this disclosure. Nomenclature for radical substituents is derived by first indicating the functionality having the point of attachment with a hyphen, followed by the adjacent functionality toward the terminal portion of the side chain, as in, e.g.:

—(C$_{1-6}$)alkyl-C(O)NH—(C$_{1-6}$)alkyl-Ph or by describing the terminal portion of the side chain first, followed by the adjacent functionality toward the point of attachment, as in, e.g.:

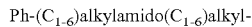
Ph-(C$_{1-6}$)alkylamido(C$_{1-6}$)alkyl-either of which refers to a radical of the formula:

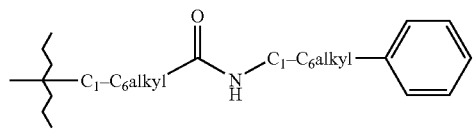

Compounds exemplified in the present invention were named according to nomenclature well known in the art, either using Autonom (ChemDraw Ultra® Version 6.0.2 Nov. 9, 2000; CambridgeSoft.com, Cambridge, Mass., www.camsoft.com, 1985–2000) or using ACD/Index Name™ (brand of commercial nomenclature software marketed by Advanced Chemistry Development, Inc., Toronto, Ontario).

Pharmaceutical Preparations & Methods of Use

Pharmaceutical compositions according to the invention may, alternatively or in addition to a compound of Formula I, comprise as an active ingredient a pharmaceutically acceptable salt of a compound of Formula I or a prodrug or pharmaceutically active metabolite of such a compound or salt.

Compositions in accordance with the invention inhibit the kinase activity of CDK/cyclin complexes. Preferred compositions of the invention contain compounds having an inhibition constant against CDK1 and/or CDK2 of about 25 µM or less, more preferably of about 10 µM or less, even more preferably of about 1 µM or less, and most preferably of about 0.5 µM or less.

Certain compounds of the Formula I may exist in various stereoisomeric or tautomeric forms. The present invention encompasses all such CDK-inhibiting compounds, including active compounds in the form of essentially pure enantiomers, racemic mixtures, and tautomers.

The compounds of the present invention may be present in the form of pharmaceutically acceptable salts. For use in medicines, the salts of the compounds of this invention refer to non-toxic "pharmaceutically acceptable salts." FDA approved pharmaceutically acceptable salt forms (Ref. International J. Pharm. 1986, 33, 201–217; J. Pharm. Sci., January, 1977, 66(1), p1) include pharmaceutically acceptable acidic/anionic or basic/cationic salts.

Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, calcium gluconate, calcium hydroxide, chloroprocaine, choline, choline bicarbonate, choline chloride, cyclohexylamine, diethanolamine, ethylenediamine, lithium, LiOMe, L-lysine, magnesium, meglumine, NH$_3$, NH$_4$OH, N-methyl-D-glucamine, piperidine, potassium, potassium-t-butoxide, potassium hydroxide (aqueous), procaine, quinine, SEH, sodium, sodium carbonate, sodium-2-ethylhexanoate, sodium hydroxide, triethanolamine (TEA) or zinc.

The term "prodrug" refers to a metabolic precursor of a compound of Formula I (or a salt thereof), that is pharmaceutically acceptable. A prodrug may be inactive when administered to a subject but is converted in vivo to an active compound. The term "active metabolite" refers to a metabolic product of a compound that is pharmaceutically acceptable and effective.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, 3$^{rd}$ Edition, John Wiley & Sons, 1999. The protecting groups may be removed at a convenient subsequent stage using methods known in the art.

The compounds of the present invention are cyclin dependent kinase inhibitors useful in a method for treating or ameliorating a cyclin dependent kinase mediated disorder. For embodiments of the present invention, the cyclin dependent kinase is selected from cyclin dependent kinase-1 or cyclin dependent kinase-2.

The cell division cycle is one of the most fundamental processes in biology which ensures the controlled proliferation of cells in multicellular organisms. Under normal growth conditions, cell proliferation is tightly regulated in response to diverse intracellular and extracellular signals. This is achieved by a complex network of proto-oncogenes and tumor-suppressor genes that are components of various signal transduction pathways. Activation of a proto-oncogene and/or a loss of a minor suppressor gene can lead to the unregulated activity of the cell cycle machinery. This, in turn, will lead to unregulated cell proliferation and to the accumulation of genetic errors which ultimately will result in the development of cancer (Pardee, A. B., *Science,* 1989, 246:603–608). In the eukaryotic cell cycle a key role is played by the cyclin dependent kinases. CDK complexes are formed via the association of a regulatory cyclin subunit and a catalytic kinase subunit. In mammalian cells, the combination of the kinase subunits (such as CDK1, CDK2, CDK4 or CDK6) with a variety of cyclin subunits (such as cyclin A, B, D1, D2, D3 or E) results in the assembly of functionally distinct kinase complexes. The coordinated activation of these complexes drives the cells through the cell cycle and ensures the fidelity of the process (Draetta, G., *Trends Biochem. Sci.,* 1990, 15:378–382; Sherr, C. J., *Cell,* 1993, 73:1059–1065). Each step in the cell cycle is regulated by a distinct and specific cyclin-dependent kinase. Regulation occurs at the boundaries of the G1/S and G2/M phases, two major transition points of the cell cycle. For example, complexes of CDK4 and D-type cyclins govern the early G1 phase of the cell cycle, while the activity of the CDK2/cyclin E complex is rate limiting for the G1 to S-phase transition. The CDK2/cyclin A kinase is required for the progression through S-phase and the CDK1/cyclin B complex controls the entry into M-phase (Sherr, 1993). A key regulator of these transitions is CDK1 kinase, a universal intracellular factor which triggers the G2/M transition of the cell cycle in all organisms. Both biochemical and genetic evidence have shown that CDK1 is the primary activity required for a cell to enter mitosis in all eukaryotic cells. In late G2, it is present as an inactive complex of CDK1 and cyclin B. In M phase, it is activated and thereafter displays kinase activity. CDK1 is known to phosphorylate a number of proteins including histone H1, DNA polymerase alpha, RNA polymerase II, retinoblastoma tumor suppressor protein (RB), p53, nucleolin, cAbI and lamin A. The kinase activity of CDK1 is required for entry of cells into mitosis, i.e., for passage from the G2 phase of the cell cycle into the M phase (Lee M. and Nurse P., *Trends Genet.,* 1988, 4:289–90; Dunphy W. G., Brizuela L., Beach D. and Newport J., *Cell,* 1988, 54:423–431; Gautier J., Norbury C., Lohka M., Nurse P. and Maller J., *Cell,* 1988, 54:433–439; Cross F., Roberts J. and Weintraub H., *Ann. Rev. Cell Biol.,* 1989, 5:341–395; Hunt, T. and Sherr, C., *Curr. Opinion Cell Biol.,* 1989, 1:268–274; and, Nurse, P., *Nature,* 1990, 344:503–508). Therefore, using cyclin dependent kinase inhibitors for tumor therapy has the potential for inhibiting tumor growth or controlling unregulated cell proliferation.

Many conventional cytotoxic cancer therapies destroy the rapidly dividing epithelium of the hair follicle and induce alopecia (hair loss). Inhibition of cyclin dependent kinases during conventional chemotherapy may represent a therapeutic strategy for prevention of chemotherapy-induced alopecia by arresting the cell cycle and reducing the sensitivity of epithelial cells to antitumor agents (Davis S. T., etal., Prevention of chemotherapy-induced alopecia in rats by CDK inhibitors, *Science, Jan.* 5, 2001, 291, 5501, 25–6). Accordingly, to be useful in a method for the prevention of chemotherapy-induced alopecia, a CDK inhibitor compound would have to be cytostatic rather than cytotoxic and be able to hold the cell in a stationary growth phase, thus protecting a hair follicle from the cytotoxic activity of a conventional chemotherapeutic agent being administered at the same time. In this way, topical application of non-apoptotic CDK inhibitors represents a potentially useful approach for the prevention of chemotherapy-induced alopecia in cancer patients.

Although coronary angioplasty is a highly effective procedure used to reduce the severity of coronary occlusion, its long-term success is limited by a high rate of restenosis. Vascular smooth muscle cell activation, migration and proliferation is largely responsible for restenosis following angioplasty (Ross, R., *Nature,* 1993, 362, 801–809). Recent studies have shown that CDK2 is activated very early after endothelial denudation in a rat carotid artery model of restenosis (Wei, G. L., et al., *Circ. Res.,* 1997, 80, 418–426). Therefore, antiproliferative therapies targeted to cyclin dependent kinases or other components of the cell cycle machinery may be a suitable approach to treat these disorders. One aspect for use of the compounds of the present invention is a method for the treatment or amelioration of restenosis wherein a CDK inhibitor is impregnated on the surface of an angioplasty balloon or stent, thus targeting drug delivery to the local environment where endothelial and smooth muscle cell proliferation are the leading cause of vascular occlusion following an initial angioplasty and restenosis in the area of a stent's implantation (Eric E. Brooks, Nathanael S. Gray, Alison Joly, Suresh S. Kerwar, Robert Lum, Richard L. Mackman, Thea C. Norman, Jose Rosete, Michael Rowe, Steven R. Schow, Peter G. Schultz, Xingbo Wang, Michael M. Wick and Dov Shiffman, CVT-313, a Specific and Potent Inhibitor of CDK2 That Prevents Neointimal Proliferation, *J. Biol. Chem.,* 1997, 272(46):29207–29211).

An embodiment of the present invention includes a prophylactic and therapeutic method for treating or ameliorating a cyclin dependent kinase mediated disorder in a subject in need thereof comprising administering to the subject a therapeutically effective amount of a compound of Formula (I) or composition thereof.

In an embodiment of the invention, the mediated kinase is a cyclin dependent kinase. In a specific embodiment, the CDK is selected from CDK-1 or CDK-2. The therapeutically effective amount of the compounds of Formula (I) exemplified in such a method is from about 0.001 mg/kg/day to about 300 mg/kg/day.

The term "subject" as used herein, refers to an animal, preferably a mammal, most preferably a human, who has been the object of treatment, observation or experiment and is at risk of (or susceptible to) developing a disease or disorder or having a disease or disorder related to unregulated CDK-1 or CDK-2 activity.

The term "prophylactic" refers to a method for preventing a cyclin dependent kinase mediated disorder in a subject in need thereof comprising administering to the subject an effective amount of a compound of Formula (I) or a composition thereof.

The term "therapeutically effective amount" or "prophylactically effective amount," as used herein, means that amount of active compound or pharmaceutical agent that elicits the biological or medicinal response (such as inhibiting activation of a CDK) in a tissue system, animal or human, that is being sought by a researcher, veterinarian, medical doctor, or other clinician, which includes alleviation of the symptoms of the disease or disorder being treated.

Another aspect of the present invention includes the use of a compound of Formula (I) for the preparation of a medicament for preventing, treating or ameliorating a cyclin dependent kinase mediated disorder in a subject in need thereof.

In accordance with the method of the present invention, an individual compound of the present invention or a composition thereof can be administered at different times during the course of therapy or concurrently in divided or single combination forms. Prophylactic administration can occur prior to the manifestation of symptoms characteristic of a cyclin dependent kinase associated disease or disorder such that the disease or disorder is prevented or, alternatively, delayed in its progression. The instant invention is therefore to be understood as embracing all such regimes of simultaneous or alternating treatment and the term "administering" is to be interpreted accordingly.

The term "cyclin dependent kinase mediated disorder" as used herein, includes, and is not limited to disorders and diseases associated with cyclin dependent kinase overactivity and conditions that accompany such diseases. Cyclin dependent kinase overactivity includes unregulated cellular mitosis, unregulated cell proliferation and upregulated cyclin dependent kinase activity. Disorders and diseases associated with unregulated cell proliferation include cancers (such as glioma cancers, lung cancers, breast cancers, colorectal cancers, prostate cancers, gastric cancers, esophageal cancers, leukemias and lymphomas), and associated pathologies such as abnormal cell proliferation, tumor growth, tumor vascularization, as well as angiopathy, angiogenesis, and chemotherapy-induced alopecia. Disorders and diseases associated with unregulated cellular mitosis, unregulated cell proliferation and upregulated cyclin dependent kinase activity include atherosclerosis, transplantation-induced vasculopathies, neointima formation, lung fibrosis, pulmonary fibrosis, glomerulonephritis, glomerulosclerosis, congenital multicystic renal dysplasia, kidney fibrosis, diabetic retinopathy, rheumatoid arthritis and restenosis.

The term "upregulated cyclin dependent kinase activity" refers to either:

increased or unregulated CDK activity or expression, increased CDK expression leading to unwanted cell proliferation, or mutations leading to constitutive activation of CDK.

The existence of an inappropriate or abnormal level or activity of CDK is determined by procedures well known in the art.

The term "disorders and diseases associated with unregulated cell proliferation" refers to disorders wherein unwanted cell proliferation of one or more subset of cells in a multicellular organism occurs resulting in harm (such as discomfort or decreased life expectancy) to the multicellular organism. Such cell proliferative disorders can occur in different types of animals and humans and include, but are not limited to, cancers (glioma, lung, breast, colorectal, prostate, gastric and esophageal, leukemias and limphomas), atherosclerosis, restenosis, psoriasis, papilloma, pulmonary fibrosis, instent stenosis, vascular graft restinosis, glomerular nephritis, diabetic retinopathy and rheumatoid arthritis.

Another aspect of the present invention includes a method for inhibiting a cell's unregulated entry into mitosis comprising administering to the cell an effective amount of a compound of Formula (I) or composition thereof for inhibiting cyclin dependent kinase activity in the cell.

Another aspect of the present invention includes a method for inhibiting unregulated cell proliferation in a tumor comprising administering to the tumor an effective amount of a compound of Formula (I) or composition thereof for inhibiting cyclin dependent kinase activity in the tumor.

Another aspect of the present invention includes a method for downregulating cyclin dependent kinase activity in a cell comprising administering to the cell an effective amount of a compound of Formula (I) or composition thereof for downregulating cyclin dependent kinase activity in the cell.

Another aspect of the present invention includes a method for treating or ameliorating chemotherapy induced alopecia in a subject in need thereof comprising topically administering to the subject a therapeutically effective amount of a compound of Formula (I) or composition thereof.

Another aspect of the present invention includes a method for use of a compound of Formula (I) or composition thereof advantageously administered in one or more cell anti-proliferation therapies including chemotherapy, radiation therapy, gene therapy or immunotherapy for preventing, treating or ameliorating a cyclin dependent kinase mediated disorder.

The combination therapy is selected from, e.g., co-administration of a compound of Formula (I) or composition thereof and a chemotherapeutic agent for preventing, treating or ameliorating a cyclin dependent kinase mediated disorder, sequential administration of a compound of Formula (I) or composition thereof and a chemotherapeutic agent for preventing, treating or ameliorating a cyclin dependent kinase mediated disorder, administration of a composition containing a compound of Formula (I) and a chemotherapeutic agent for preventing, treating or ameliorating a cyclin dependent kinase mediated disorder, or, simultaneous administration of a separate composition containing a compound of Formula (I) and a separate composition containing a chemotherapeutic agent for preventing, treating or ameliorating a cyclin dependent kinase mediated disorder.

For example, the compounds of this invention may be useful in combination therapies with a chemotherapeutic agent for the treatment of a number of different cancers and advantageously may facilitate the use of a reduced dose of the chemotherapeutic agent that is recommended for a particular cancer or cell proliferation disorder. Therefore, it is contemplated that the compounds of this invention can be used during or after treatment with a particular chemotherapeutic agent. The term "chemotherapeutic agent" includes, and is not limited to, anti-angiogenic agents, anti-tumor agents, cytotoxic agents, inhibitors of cell proliferation, and the like. The term "treating or ameliorating" includes, and is not limited to, facilitating the eradication of, inhibiting the progression of or promoting stasis of a malignancy.

Another aspect of the present invention includes a method for administering a compound of the present invention in combination with radiation therapy. As used herein, "radiation therapy" refers to a therapy that comprises exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

The composition may take a wide variety of forms to effectuate mode of administration, including, but not limited to, intravenous (both bolus and infusion), oral, nasal, transdermal, topical with or without occlusion, and injection intraperitoneally, subcutaneously, intramuscularly, intratumorally or parenterally. The composition may be in a dosage unit such as a tablet, pill, capsule, powder, granule, sterile parenteral solution or suspension, metered aerosol or liquid spray, drop, ampoule, auto-injector device or suppository; for administration orally, parenterally, intranasally, sublingually or rectally or by inhalation or insufflation. Compositions suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the composition may be presented in a form suitable for once-weekly or once-monthly administration; for example, an insoluble salt of the active compound, such as the decanoate salt, may be adapted to provide a depot preparation for intramuscular injection.

The phrase "pharmaceutically acceptable" refers to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use. In preparing the compositions in oral dosage form, one or more of the usual pharmaceutical carriers may be employed, including necessary and inert pharmaceutical excipients, such as water, glycols, oils, alcohols, flavoring agents, preservatives, coloring agents, syrup and the like; in the case of oral liquid preparations, carriers such as starches, sugars, diluents, granulating agents, lubricants, binders, disintegrating agents and the like may be employed.

The dosage unit (tablet, capsule, powder, injection, suppository, teaspoonful and the like) containing the pharmaceutical compositions herein will contain an amount of the active ingredient necessary to deliver a therapeutically effective amount as described above. The composition may contain from about 0.001 mg to about 5000 mg (preferably, from about 0.01 to about 500 mg) of the active compound or prodrug thereof and may be constituted into any form suitable for the mode of administration selected for a subject in need. A contemplated therapeutically effective amount may range from about 0.001 mg to about 300 mg/kg of body weight per day. Preferably, the range is from about 0.03 to about 100 mg/kg of body weight per day. Most preferably, the range is from about 0.05 to about 15 mg/kg of body weight per day. The compounds may be administered according to a dosage regimen of from about 1 to about 5 times per day.

For oral administration, the compositions are preferably provided in the form of tablets containing, e.g., 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. Optimal dosages will vary depending on factors associated with the particular patient being treated (e.g., age, weight, diet and time of administration), the severity of the condition being treated, the compound being employed, the mode of administration and the strength of the preparation. The use of either daily administration or post-periodic dosing may be employed.

For preparing solid compositions such as tablets, the compound may be, e.g., mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.001 to about 5000 mg of the active ingredient of the present invention. The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

For oral administration in the form of a tablet or capsule, the active drug component can be optionally combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrating agents include, without limitation, starch, methyl cellulose, agar, bentonite, xanthan gum and the like.

Lubricants such as, but not limited to, colloidal silicon dioxide (such as Aerosil® 200), talc, stearic acid, magnesium stearate, calcium stearate or silica gel, may be employed.

Coloring agents such as, but not limited to, any pharmaceutically acceptable natural or synthetic dye and the like or mixtures thereof, may be employed.

The liquid forms in which the compound of Formula (I) may be incorporated, e.g., aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds may alternatively be administered parenterally via injection of a formulation consisting of the active ingredient dissolved in an inert liquid carrier. The injectable formulation can include the compound mixed with an appropriate inert liquid carrier. Acceptable liquid carriers include vegetable oils such as peanut oil, cotton seed oil, sesame oil, and the like, as well as organic solvents such as solketal, glycerol, formal, and the like. Aqueous parenteral formulations may also be used. For example, acceptable aqueous solvents include water, Ringer's solution and an isotonic aqueous saline solution. Further, a sterile non-volatile oil can usually be employed as solvent or suspending agent in the aqueous formulation. The formulations are prepared by dissolving or suspending the active ingredient in the liquid carrier such that the final formulation contains from about 0.005 to about 10% by weight of the active ingredient. Other additives including, e.g., a preservative, an isotonizer, a solubilizer, a stabilizer and a pain-soothing agent may adequately be employed.

Advantageously, compounds of Formula (I) may be administered in a single daily dose, or the total daily dosage may be administered in divided doses of two, three or four times daily. Furthermore, compounds of the present invention can be administered in intranasal form via topical use of suitable intranasal vehicles, or via transdermal routes, using, e.g., those forms of transdermal skin patches well known to those of ordinary skill in that art.

The present invention also provides methods to prepare the pharmaceutical compositions of this invention. A compound of Formula (I) as the active ingredient is intimately admixed with a pharmaceutical carrier according to conventional pharmaceutical compounding techniques, which carrier may take a wide variety of forms depending on the form of preparation desired for administration. In preparing the compositions in oral dosage form, any of the usual pharmaceutical media may be employed. For solid oral dosage forms, suitable carriers and additives include starches, sugars, diluents, granulating agents, lubricants, binders, disintegrating agents and the like. For liquid oral preparations, suitable carriers and additives include water, glycols, oils, alcohols, flavoring agents, preservatives, coloring agents and the like. Additionally, liquid forms of the active drug component can be combined in suitably flavored suspending or dispersing agents such as the synthetic and natural gums, including for example, tragacanth, acacia, methyl-cellulose and the like. Other dispersing agents that may be employed include glycerin and the like.

The terms used in describing the invention are commonly used and known to those skilled in the art. As used herein, the following abbreviations have the indicated meanings:

| | |
|---|---|
| "Ph" or "PH" | Phenyl |
| "BINAP" | 2,2'-Bis(diphenylphosphino)-1,1'-binaphthyl |
| "Bn" | Benzyl |
| "Me" | Methyl |
| "Et" | Ethyl |
| "Py" | Pyridine |
| "Cpd" | Compound |
| "DIC" | 1,3-Diisopropyl carbodiimide |
| "EDIC" | 1-(3-Dimethylaminopropyl)-3-ethylcarbodiimide |
| "HOBt" | 1-Hydroxybenzotriazole |
| "THF" | Tetrahydrofuran |
| "DMF" | N,N-Dimethyl formamide |
| "DMSO" | Dimethyl sulfoxide |
| "LDA" | Lithium diisopropylamide |
| "Pd$_2$(dba)$_3$" | Tris(dibenzylideneacetone)dipalladium(0) |
| "DPPF" | 1,1'-Bis(diphenylphosphini)ferrocene |
| "TFA" | Trifluoroacetic acid |
| "TMEDA" | Tetramethylethylenediamine |

General Synthetic Methods

Representative compounds of the present invention can be synthesized in accordance with the general synthetic methods described below, which are illustrated more particularly in the schemes that follow. The invention should not be construed as being limited by the chemical reactions and conditions expressed. The preparation of the various starting materials used in the schemes is well within the skill of persons versed in the art.

Scheme A

In accordance with Scheme A, a lithiation agent (such as n-butyl lithium, t-butyl lithium and the like) was slowly added to a cold solution of Compound A1 (prepared as described by Zimmerman, S C, et al., *J. Org. Chem.*, 1993, 58, 6625), wherein PG represents a protecting group (such as pivoloyl, Boc and the like), in a suitable solvent (such as t-butyl methyl ether, THF and the like). The mixture was warmed and stirred. Compound A2 (wherein $R_3$ is as defined herein and X is a leaving group such as halogen; wherein, when $R_3$ is a reactive substituent, the substituent is blocked with any well-known protecting group) was then added and the mixture was cooled and stirred. The mixture was then neutralized with acid and extracted with a suitable solvent (such as methylene chloride) to provide a Compound A3.

Compound A3 was dissolved in a suitable solvent (such as dioxane, methylene chloride and the like). When PG on Compound A3 was a pivoloyl group, the mixture was cooled, a KOH solution was added and the mixture was heated to reflux. When PG on Compound A3 was a Boc group, the mixture was cooled, TFA was added and the mixture was stirred at room temperature. The mixture was then purified to yield a Compound A4 (wherein $R_1$ is hydrogen).

Compound A4 was then dissolved in a suitable solvent (such as dioxane) and a catalyst (such as Pd$_2$(dba)$_3$), a ligand (such as BINAP), a base (such as cesium carbonate) and Compound A5 (where $R_1$ is as defined herein and X is a leaving group such as halogen, triflate and the like; and, when $R_1$ is a reactive substituent, the substituent is blocked with any well-known protecting group) were added. The resulting mixture was heated, cooled, then water was added and the mixture was extracted with a suitable solvent (such as methylene chloride) to yield Compound A6.

In particular, to prepare compounds wherein $R_1$ was substituted C(O), a Compound A7 (wherein $R_{1a}$ is alkyl, aryl or heteroaryl optionally substituted with one to two substituents and X is a leaving group such as halogen; and, when $R_{1a}$ is a reactive substituent, the substituent is blocked with any well-known protecting group) was added to the solution of Compound A4 in the presence of a base (such as triethyl amine). The resulting mixture was stirred at room temperature, then water was added and the mixture was extracted with a suitable solvent (such as methylene chloride). The crude product was purified via chromatography to yield Compound A8.

In particular, to prepare compounds wherein $R_1$ was a substituted urea, a Compound A9 (wherein $R_{1b}$ is alkyl, aryl or heteroaryl optionally substituted with one to two substituents and Y is either O or S) was added to the solution of Compound A4 in a suitable solvent (such as DMF) and in the presence of a base (such as potassium t-butoxide). The resulting mixture was stirred, then water was added and the mixture was extracted with a suitable solvent (such as ethyl acetate) to yield Compound A10.

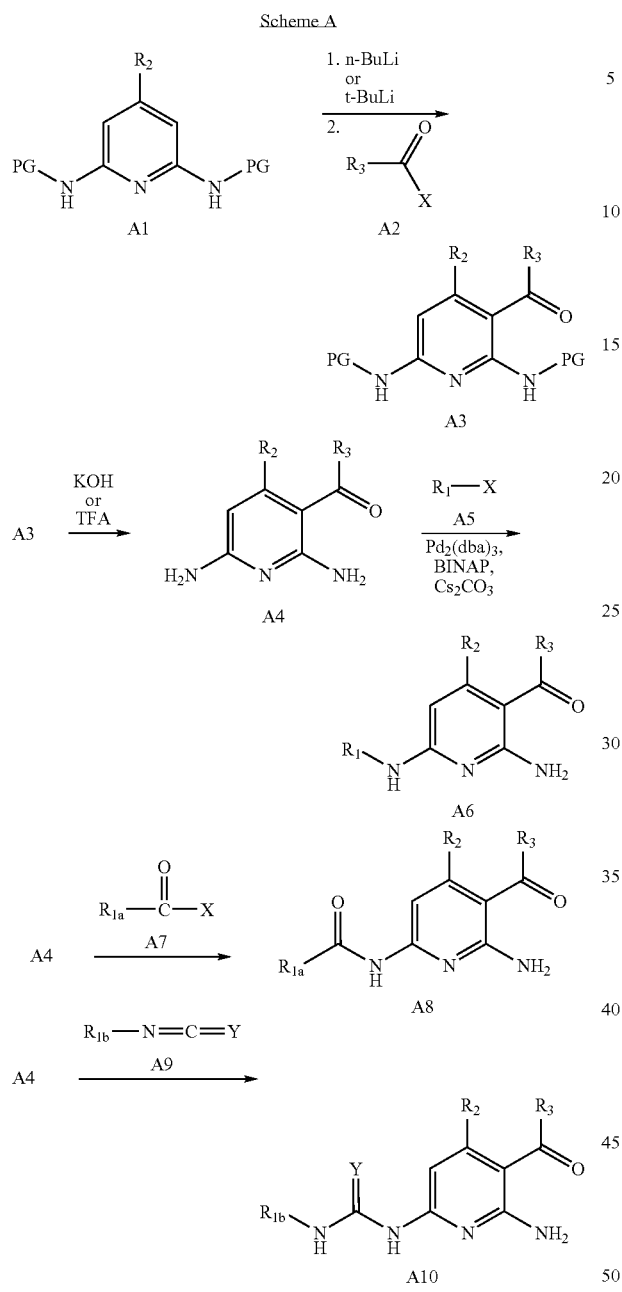

Scheme B

In accordance with Scheme B, a BBr$_3$ solution in a suitable solvent (such as methylene chloride) was added to a solution of Compound B1 (wherein R$_1$ is a substituted ring system such as phenyl substituted with dibenzyl (Bn) aminosulfonyl) in a suitable solvent (such as methylene chloride). The reaction mixture was refluxed and evaporated to dryness, resulting in the removal of one of the two N-benzyl protecting groups. The dried residue was re-dissolved in a mixture of acetic acid and aqueous HI (58% by weight), then refluxed and evaporated to dryness. The residue product was partitioned between a solution of an aqueous base such as saturated aqueous sodium bicarbonate and an organic solvent such as methylene chloride, then extracted with methylene chloride. The organic layers were combined, dried, concentrated and purified to give a Compound B2.

Alternatively, when other protecting groups are used, as in a Boc-protected Compound B3 (wherein R$_1$ is a substituted ring system such as phenyl substituted with Boc-aminosulfonyl), the compound was treated with a deprotection reagent such as TFA in a suitable solvent (such as methylene chloride). The reaction mixture was evaporated to dryness and purified via column chromatography to give Compound B2.

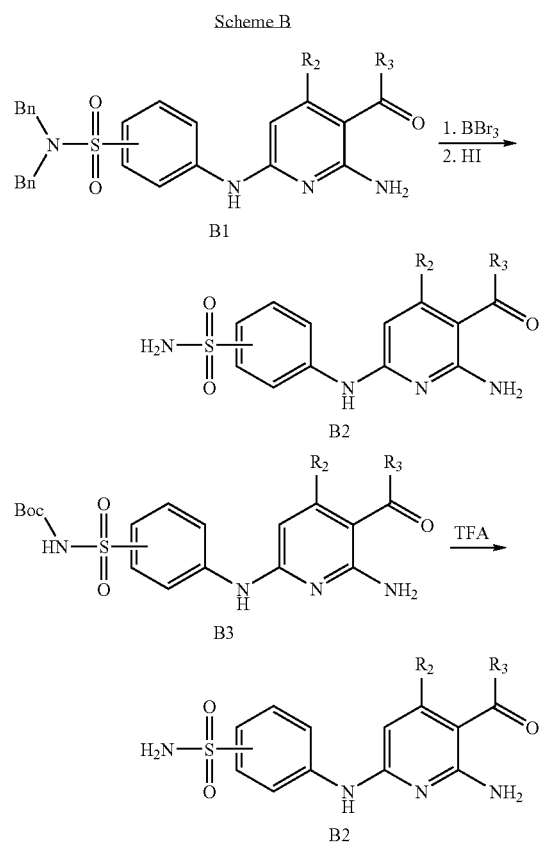

Scheme C

A Compound C1 (wherein R$_1$ is a ring system such as cyano substituted phenyl) was hydrolyzed (as described by Larock, R C., Comprehensive Organic Transformations, VCH Publishers, New York, 1989, 993–994) to provide a mixture of a Compound C2 and a Compound C3.

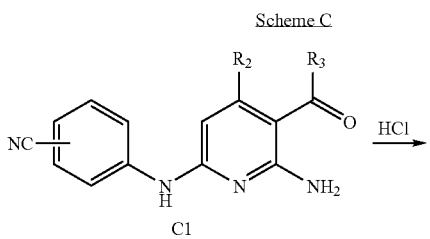

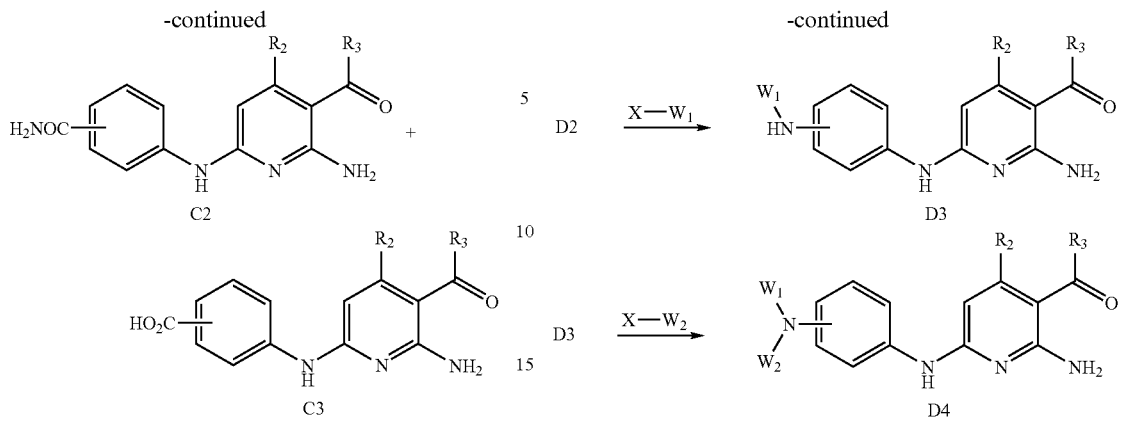

Scheme D

A Compound D1 (wherein $R_1$ is a ring system such as nitro substituted phenyl) was reduced using Pd-catalyzed hydrogenation (as described in Larock, supra, 411–415) to provide a Compound D2. In certain instances, a particular reagent (such as ammonium formate used in Example 5) will yield a mixture of a Compound D2 as a major product and a Compound D2a as a minor product. The terminal amino group on a Compound D2 may be further mono or disubstituted (such as with a $W_1$ or $W_2$ substituted X group; wherein $W_1$ and $W_2$ are independently alkyl, C(O)alkyl, C(O)aryl, $SO_2$alkyl, $SO_2$amino or $SO_2$aryl and X is halogen) using reductive amination (as described in Larock, supra, 421–425), alkylation (as described in Larock, supra, 397–406) or acylation (as described in Larock, supra, 972–976) to prepare Compound D3 and further to prepare Compound D4. or on a Compound D2 and Compound D2a in a mixture.

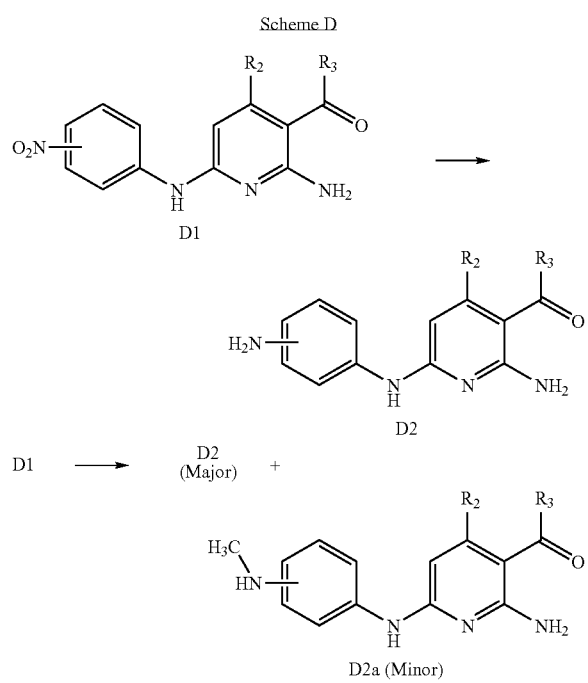

Scheme D

Specific Synthetic Methods

Specific compounds which are representative of this invention were prepared as per the following examples and reaction sequences. The examples and the diagrams depicting the reaction sequences are offered by way of illustration to aid in the understanding of the invention and should not be construed in any way to limit the invention. The depicted intermediates may also be used in subsequent examples to produce additional compounds of the present invention. No attempt has been made to optimize the yields obtained in any of the reactions.

General: $^1H$ and $^{13}C$ NMR spectra were measured on a Bruker AC-300 (300 MHz) spectrometer using tetramethylsilane and the deuterated solvent respectively as internal standards. Elemental analyses were obtained by Quantitative Technologies Inc. (Whitehouse, N.J.) and the results were within 0.4% of the calculated values unless otherwise mentioned. Melting points were determined in open capillary tubes with a Mel-Temp II apparatus (Laboratory Devices Inc.) and were uncorrected. Electrospray mass spectra (MS-ES) were recorded on a Hewlett Packard 59987A spectrometer. High resolution mass spectra (HRMS) were obtained on a Micromass Autospec. E spectrometer by fast atom bombardment (FAB) technique.

EXAMPLE 1

(2,6-diamino-3-pyridinyl)(2,6-difluorophenyl)methanone (Compound 1)

n-Butyl lithium (1.6 M in hexane, 23.3 mL, 37.3 mmol) was added dropwise to a solution of a N-[3-(2,6-difluorobenzoyl)-6-[(2,2-dimethyl-1-oxopropyl)amino]-2-pyridinyl]-2,2-dimethylpropanamide Compound A1 (prepared as described in Scheme A) in anhydrous t-butyl methyl ether (35 mL) and TMEDA (1.5 mL) at a temperature of about −15° C. The mixture was then stirred at a temperature of between about 0 to about 15° C. for about 16 hours.

A 2,6-difluorobenzoyl chloride Compound 1a was added quickly and the mixture was stirred at a temperature of between about 0 to about −5° C. for about 3 hours. The mixture was then neutralized with 2N HCl and extracted with methylene chloride (5×100 mL). The organic layers were combined, dried and evaporated then separated by chromatography (on silica gel, eluting with 1:2 ethyl acetate: hexane) to give a N-[3-(2,6-difluorobenzoyl)-6-[(2,2-dimethyl-1-oxopropyl)amino]-2-pyridinyl]-2,2-dimethylpropanamide Compound 1b (2.63 g, 54% yield) as a white powder. ¹H NMR (300 MHz, CDCl₃) δ 11.9 (s, br, 1H), 9.0 (s, br, 1H), 8.10–7.40 (m, 3H), 1.45 (s, 6H), 1.32 (s, 12H); MS (ESI) m/z: 418 (M+H⁺), 440 (M+Na⁺).

2N KOH solution (3 mL) was added dropwise to a solution of Compound 1b (160 mg, 0.38 mmol) in dioxane (3 mL) at about −15° C. The reaction mixture was heated to reflux for about 6 hours, then cooled to room temperature and extracted with methylene chloride (4×20 mL). The organic layers were combined, dried, evaporated and separated by chromatography (on silica gel, eluting with 5% methanol/methylene chloride) to give Compound 1 (86 mg, 69% yield) as a yellow powder. MS (ESI) m/z: 250 (M+H⁺),

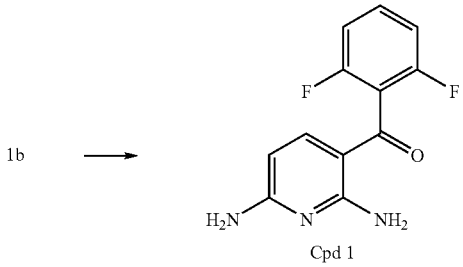

Using the procedure of Example 1, other compounds of the present invention were prepared:

| Cpd | Name | Materials |
|---|---|---|
| 2 | (2,6-diamino-3-pyridinyl)(2-fluorophenyl)methanone<br>¹H NMR(300 MHz, CDCl₃) δ 7.40(m, 3H), 7.18 (m, 2H), 5.76(d, J=8.3Hz, 1H); MS(ESI)m/z: 232.0(M+H⁺), 254.1(M+Na⁺) | Follow n-BuLi reaction of Compound A1 and 2-fluorobenzoyl chloride (in place of Compound 1a) with KOH-mediated hydrolysis |
| 3 | (2,6-diamino-3-pyridinyl)phenylmethanone<br>¹H NMR(300 MHz, CDCl₃) δ 7.50(m, 6H), 5.76 (d, J=8.5Hz, 1H); MS(ESI)m/z: 214.1(M+H⁺), 236.1(M+Na⁺) | Follow reaction of Compound A1 and benzoyl chloride with KOH-mediated hydrolysis |
| 4 | (2,6-diamino-3-pyridinyl)-2-furylmethanone<br>¹H NMR(300 MHz, CDCl₃) δ 8.25(d, J=8.7Hz, 1H), 7.61(s, 1H), 7.10(d, J=3.2Hz, 1H), 6.55(s, 1H), 5.87(d, J=8.3Hz, 1H); MS(ESI) m/z: 204.1(M+H⁺), 226.0(M+Na⁺) | Follow reaction of Compound A1 and 2-furoyl chloride with KOH-mediated hydrolysis |
| 5 | (2,6-diamino-3-pyridinyl)-2-thienylmethanone<br>¹H NMR(300 MHz, CDCl₃) δ 7.96(d, J=8.6Hz, 1H), 7.58(m, 1H), 7.46(m, 1H), 7.11(m, 1H), 5.84(d, J=8.6Hz, 1H); MS(ESI)m/z: 220.0(M+H⁺) | Follow reaction of Compound A1 and 2-thienoyl chloride with KOH-mediated hydrolysis |

272 (M+Na⁺); m.p. 179–181° C.; ¹H NMR (300 MHz, CD₃OD) δ 7.49 (m, 1H), 7.10 (m, 3H), 5.80 (d, 1H).

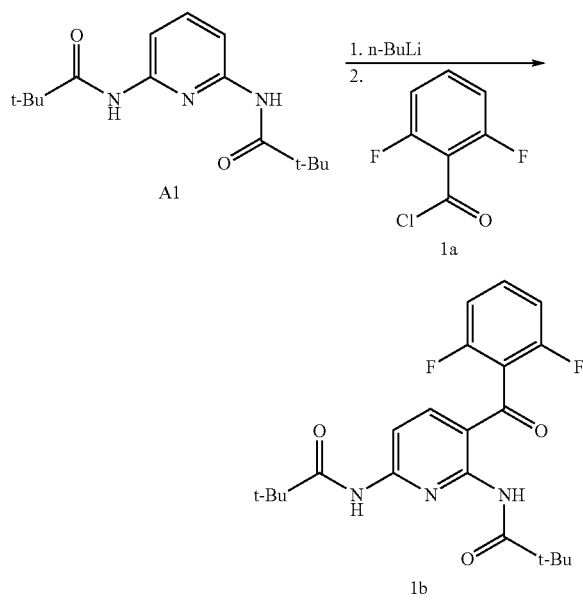

EXAMPLE 2

4-[[6-amino-5-(2,6-difluorobenzoyl)-2-pyridinyl]amino]benzenesulfonamide (Compound 6)

A N,N-Dibenzyl-4-iodobenzenesulfonamide Compound 2a (20.4 mg, 0.044 mmol), Pd₂(dba)₃ (1.0 mg), BINAP (1.8 mg) and cesium carbonate (13 mg, 0.04 mmol) were added to a solution of Compound 1 (10 mg, 0.04 mmol) in dioxane (0.20 mL) and toluene (0.25 mL). The resulting mixture was stirred in an oil-bath (at a temperature of from about 90 to about 100° C.) for about 24 hours. The mixture was cooled to rt then water (20 mL) was added and extracted with methylene chloride (4×20 mL). The organic layers were combined, dried and evaporated, then separated by chromatography (on silica gel, eluting with 1:1 ethyl acetate: hexane) to give a 4-[[6-amino-5-(2,6-difluorobenzoyl)-2-pyridinyl]amino]-N,N-bis(phenylmethyl)benzenesulfonamide Compound 2b (11 mg, 46% yield) as a yellow powder. ¹H NMR (300 MHz, CDCl₃) δ 9.0 (s, br, 2H), 7.80 (d, 2H), 7.62 (d, 2H), 7.40–7.58 (m, 2H), 7.35–6.95 (m, 12H), 6.40 (s, br, 1H), 6.12 (d, 1H), 7.35 (s, 4H); MS (ESI) m/z: 585 (M+H⁺), 607 (M+Na⁺).

BBr₃ (2.0 mL) in methylene chloride was added to a solution of Compound 2b (20 mg, 0.034 mmol) in methylene chloride (1 mL). The mixture was refluxed for 6 hours and evaporated to dryness. The residue was re-dissolved in acetic acid (1 mL) and aqueous HI (58 wt %, 1 mL) and the mixture was refluxed for 4 hours, then evaporated to dryness. The resultant residue was partitioned between saturated aqueous sodium bicarbonate and methylene chloride, then extracted with methylene chloride.

The organic layers were combined, dried and concentrated, then subjected to chromatographic purification to give Compound 6 (3.6 mg, 21% yield) as a pale yellow foam. $^1$H NMR (300 MHz, CD$_3$OD) δ 8.10 (d, 2H), 7.85 (d, 2H), 7.55 (m, 1H), 7.35 (d, 1H), 7.15 (t, 2H), 6.15 (d, 1H); MS (ESI) m/z: 405 (M+H$^+$), 427 (M+Na$^+$).

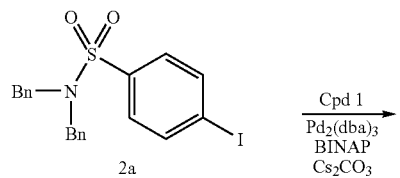

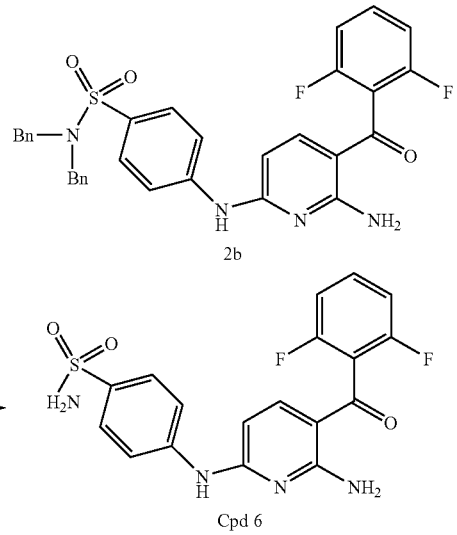

Using the procedure of Example 2, other compounds of the present invention were prepared:

| Cpd | Name | Materials |
|---|---|---|
| 7 | 4-[[6-amino-5-(2,6-difluorobenzoyl)-2-pyridinyl]amino]-N,N-dimethylbenzenesulfonamide (63% yield)$^1$H NMR(300 MHz, CDCl$_3$) δ 8.8(s, br, 2H), 7.70(m, 4H), 7.30–7.48(m, 3H), 6.98(t, 2H), 6.08(d, 1H), 6.72 and 6.75(each s, each 3H); MS (ESI)m/z: 433(M+H$^+$) | Use N,N-dimethyl-4-iodobenzenesulfonamide Compound 8a in place of Compound 2a |
| 8 | 4-[[6-amino-5-(2,6-difluorobenzoyl)-2-pyridinyl]amino]benzonitrile (66% yield)m.p. 208–210° C.(decomposed); $^1$H NMR (300 MHz, CD$_3$OD) δ 8.15(d, 2H), 7.65(d, 2H), 7.55 (m, 1H), 7.35(d, 1H), 7.10(t, 2H), 6.12(d, 1H); MS (ESI)m/z: 351(M+H$^+$), 373(M+Na$^+$) | Use 4-iodobenzonitrile in place of Compound 2a |
| 9 | [2-amino-6-[(4-nitrophenyl)amino]-3-pyridinyl](2,6-difluorophenyl)methanone (yellow solid, 68% yield)m.p. 220–225° C. (decomposed); $^1$H NMR(300 MHz, CDCl$_3$) δ 8.9(s, 2H), 8.25(d, 2H), 7.75(d, 2H), 7.55–7.40(m, 2H), 7.05(t, 2H), 6.12(d, 1H), 5.7(s, 1H); MS(ESI)m/z: 371(M+H$^+$), 393(M+Na$^+$) | Use 1-iodo-4-nitrobenzene in place of Compound 2a |
| 10 | [2-amino-6-[(3-nitrophenyl)amino]-3-pyridinyl](2,6-difluorophenyl)methanone (90% yield)$^1$H NMR(300 MHz, CD$_3$OD) δ 8.70(t, J=4.3Hz, 1H), 8.26(m, 1H), 7.86(m, 1H), 7.66(d, J=7.6Hz, 1H), 7.52(m, 3H), 7.29(m, 1H), 7.09(m, 2H), 6.59(m, 1H), 6.05(d, J=8.8Hz, 1H); MS(ESI) m/z: 371.0(M+H$^+$) | Use 1-iodo-3-nitrobenzene in place of Compound 2a |
| 11 | [2-amino-6-[(3-chlorophenyl)amino]-3-pyridinyl](2,6-difluorophenyl)methanone (47% yield)$^1$H NMR(300 MHz, CD$_3$OD) δ 7.93–6.98 (m, 11H), 6.00(d, J=8.8Hz, 1H); MS(ESI)m/z: 360.1(M+H$^+$) | Use 1-chloro-3-iodobenzene in place of Compound 2a |
| 12 | [2-amino-6-[(2-nitrophenyl)amino]-3-pyridinyl](2,6-difluorophenyl)methanone (59% yield) $^1$H NMR(300 MHz, CD$_3$OD) δ 8.65(dd, J=1.3Hz, 8.5Hz, 1H), 8.14(dd, J=1.5, 8.4Hz, 1H), 7.67(m, 1H), 7.53(m, 1H), 7.37(m, 2H), 7.19 | Use 1-iodo-2-nitrobenzene in place of Compound 2a |

| Cpd | Name | Materials |
|---|---|---|
| | (m, 2H), 7.10(m, 3H), 6.19(d, J=8.7Hz, 1H); MS (ESI)m/z: 371.0(M+H⁺) | |

EXAMPLE 3

[2-amino-6-(phenylamino)-3-pyridinyl](2,6-difluorophenyl)methanone (Compound 13)

Compound 13 was prepared by the nucleophilic substitution of Compound 1 with iodobenzene (26% yield). ¹H NMR (300 MHz, CDCl₃) δ 7.99–6.58 (m, 10H); MS (ESI) m/z: 326.0 (M+H⁺), 339.1 (M+Na⁺).

Using the procedure of Example 3, other compounds of the present invention were prepared:

| Cpd | Name | Materials |
|---|---|---|
| 14 | [2-amino-6-(2-pyridinylamino)-3-pyridinyl](2,6-difluorophenyl)methanone (44% yield) ¹H NMR(300 MHz, CD₃OD) δ 8.26(m, 2H), 7.74(m, 1H), 7.52(m, 1H), 7.31(m, 2H), 7.09(m, 2H), 7.00 (m, 1H), 6.43(d, J=8.9Hz, 1H); MS(ESI)m/z: 327.1(M+H⁺) | Use 2-bromopyridine in place of iodobenzene |

EXAMPLE 4

4-[[6-amino-5-(2,6-difluorobenzoyl)-2-pyridinyl]amino]benzonitrile (Compound 15)

4-[[6-amino-5-(2,6-difluorobenzoyl)-2-pyridinyl]amino]benzoic acid (Compound 16)

Concentrated HCl (1 mL) was added to a suspension of Compound 8 (17 mg, 0.048 mmol) and the mixture was stirred and heated in an oil-bath at about 90° C. overnight. The mixture was then evaporated in vacuo and subjected to HPLC separation to give a mixture of Compound 15 (3.9 mg, 23% yield) and Compound 16 (4.8 mg, 27% yield).

For Compound 15: ¹H NMR (300 MHz, CD₃OD) δ 8.10 (d, 2H), 7.62 (d, 2H), 7.55 (m, 1H), 7.35 (d, 1H), 7.10 (t, 2H), 6.12 (d, 1H); MS (ESI) m/z: 369 (M+H⁺), 391 (M+Na⁺); HRFAB-MS (C₁₉H₁₅F₂N₄O₂): calcd 369.1162, found 369.1163 (M+H⁺);

For Compound 16: ¹H NMR (300 MHz, CD₃OD) δ 8.12 (d, 2H), 7.60 (d, 2H), 7.50 (m, 1H), 7.32 (d, 1H), 7.12 (t, 2H), 6.15 (d, 1H); MS (ESI) m/z: 370 (M+H⁺), 392 (M+Na⁺); HRFAB-MS (C₁₉H₁₄F₂N₃O₃): calcd 370.1017, found 370.1003 (M+H⁺).

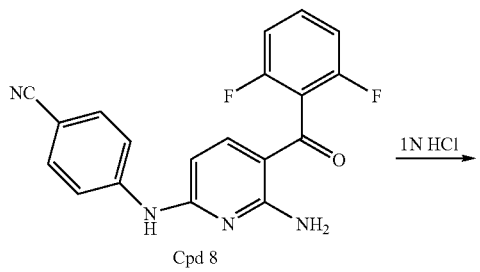

Cpd 8

1N HCl

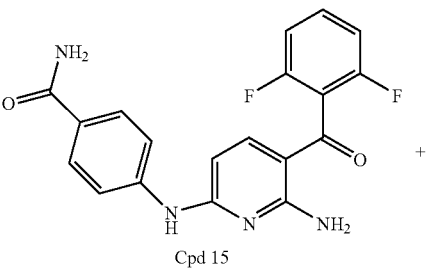

Cpd 15

+

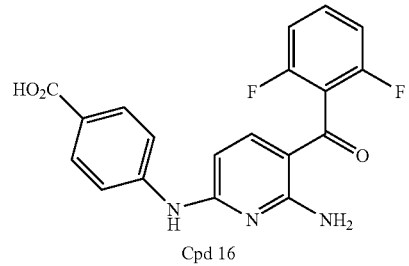

Cpd 16

EXAMPLE 5

[2-amino-6-[(4-aminophenyl)amino]-3-pyridinyl](2,6-difluorophenyl)methanone (Compound 17)

[2-amino-6-[[4-(methylamino)phenyl]amino]-3-pyridinyl](2,6-difluorophenyl)methanone (Compound 18)

Ammonium formate (100 mg, 1.6 mmol) was added to a solution of Compound 9 (16 mg, 0.043 mmol) and 10% Pd/C (5 mg) in methanol (2 mL). The resultant mixture was refluxed for 1.5 hours and concentrated. The residue was then subjected to chromatography separation (on silica gel, eluting with 1:1 ethyl acetate/hexane) to give a mixture of Compound 17 (6.8 mg, 46% yield) and Compound 18 (2.2 mg, 14% yield).

For Compound 17: ¹H NMR (300 MHz, CD₃OD) δ 7.52 (m, 1H), 7.45 (d, 2H), 7.75 (d, 2H), 7.20–7.05 (m, 3H), 6.78 (m, 2H), 5.95 (d, 1H); MS (ESI) m/z: 341 (M+H⁺), 363 (M+Na⁺);

For Compound 18: $^1$H NMR (300 MHz, CD$_3$OD) δ 7.52 (m, 1H), 7.38 (m, 2H), 7.25–7.05 (m, 3H), 6.68 (d, 2H), 5.95 (d, 1H); $^1$H NMR (CDCl$_3$) δ 8.8 (s, 2H), 7.3–7.2 (m, 3H), 7.08 (d, 2H), 7.05 (t, 2H), 6.80 (s, 1H), 6.62 (d, 2H), 5.88 (d, 1H) 2.92 (s, 3H); MS (ESI) m/z: 355 (M+H$^+$), 377 (M+Na$^+$); HRFAB-MS (C$_{19}$H$_{16}$F$_2$N$_4$O): calcd 355.1368, found 355.1370 (M+H$^+$).

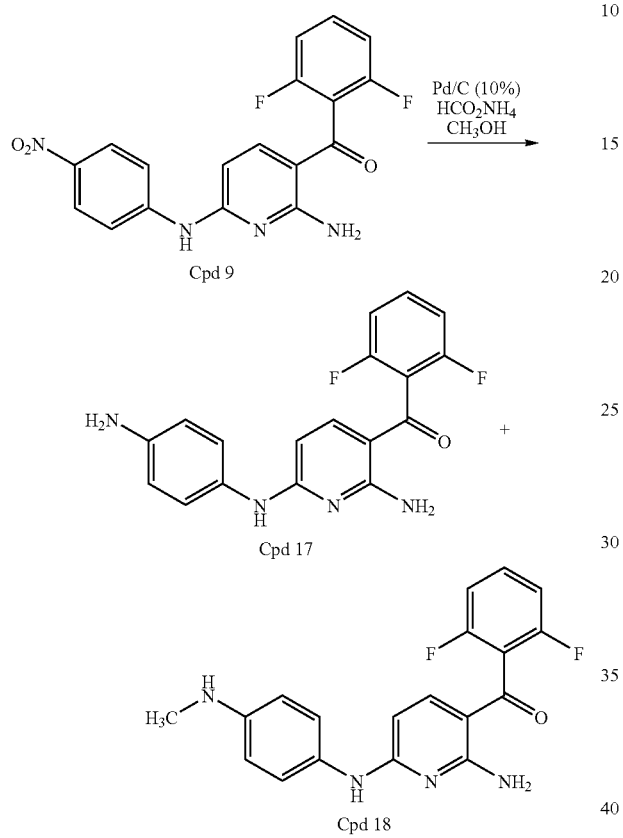

EXAMPLE 6

N-[4-[[6-amino-5-(2,6-difluorobenzoyl)-2-pyridinyl]amino]phenyl]benzenesulfonamide (Compound 19)

A solution of Compound 17 (5.8 mg, 0.017 mmol), benzenesulfonyl chloride (2.38 μL, 0.019 mmol), triethylamine (2.9 μL, 0.021 mmol) in THF (0.2 mL) and methylene chloride (0.2 mL) was stirred at rt for about 2 hours. The resultant mixture was then separated by chromatography (on silica gel, eluting with 1:1 ethyl acetate:hexane) to give Compound 19 (6 mg, 73% yield).

$^1$H NMR (300 MHz, CDCl$_3$) δ 8.8 (s, 2H), 7.75 (d, 2H), 7.68–7.30 (m, 7H), 7.20–6.90 (m, 4H), 6.65 (s, 1H), 5.95 (d, 1H), 5.50 (s, 1H); MS (ESI) m/z: 481 (M+H$^+$), 503 (M+Na$^+$).

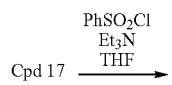

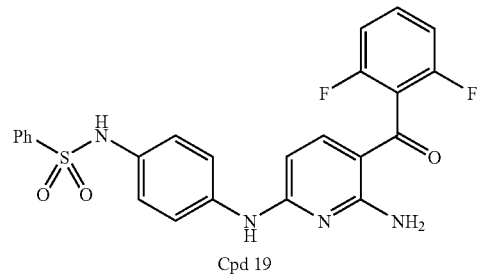

EXAMPLE 7

[2-amino-6-[(2-aminophenyl)amino]-3-pyridinyl](2,6-difluorophenyl)methanone (Compound 20)

Compound 20 was prepared using the procedure of Example 5 by palladium catalyzed hydrogenation of Compound 12 (90% yield). $^1$H NMR (300 MHz, CD$_3$OD) δ 7.48 (m, 1H), 7.10 (m, 5H), 6.86 (m, 1H), 6.72 (m, 1H), 5.84 (d, J=8.9 Hz, 1H); MS (ESI) m/z: 341.0 (M+H$^+$), 363 (M+Na$^+$).

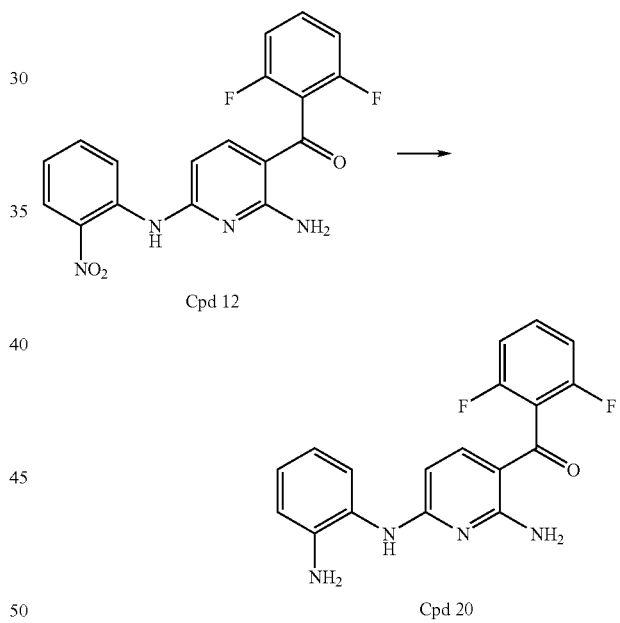

Using Compound 20 as a starting material, other compounds of the present invention were prepared:

| Cpd | Name | Materials |
| --- | --- | --- |
| 21 | N-[2-[[6-amino-5-(2,6-difluorobenzoyl)-2-pyridinyl]amino]phenyl]acetamide (82% yield)$^1$H NMR(300 MHz, CD$_3$OD) δ 7.52(m, 3H), 7.22(m, 3H), 7.07(m, 2H), 5.95(d, J=8.9Hz, 1H), 2.10(s, 3H); MS(ESI)m/z: 383.0(M+H$^+$), 405.1(M+Na$^+$) | acetyl chloride |
| 22 | N-[2-[[6-amino-5-(2,6-difluorobenzoyl)-2-pyridinyl]amino]phenyl]benzamide (99% yield)$^1$H NMR(300 MHz, CD$_3$OD) δ 7.78(m, 2H), 7.70(M, 1H), 7.54(m, 2H), | benzoyl chloride |

| Cpd | Name | Materials |
|---|---|---|
|  | 7.44(m, 3H), 7.27(m, 3H), 7.07 (m, 2H), 6.00(d, J=8.8Hz, 1H); MS(ESI)m/z: 445.1 (M+H⁺), 467.0(M+Na⁺) |  |
| 23 | N-[2-[[6-amino-5-(2,6-difluorobenzoyl)-2-pyridinyl]amino]phenyl]benzenesulfonamide (40% yield)¹H NMR(300 MHz, CD₃OD) δ 7.49(m, 5H), 7.33(m, 2H), 7.13(m, 6H), 5.72(d, J=8.9Hz, 1H), 2.10(s, 3H); MS(ESI)m/z: 481.1(M+H⁺), 503.0(M+Na⁺) | benzene-sulfonyl chloride |

EXAMPLE 8

4-[[6-amino-5-(2-fluorobenzoyl)-2-pyridinyl]amino]-N,N-dimethyl benzenesulfonamide (Compound 24)

Compound 24 was prepared by the nucleophilic substitution of Compound 2 with N,N-dimethyl-4-iodobenzenesulfonamide Compound 8a (35% yield). ¹H NMR (300 MHz, CDCl₃) δ 7.73 (s, 4H), 7.42 (m, 4H), 7.10 (m, 2H), 6.05 (d, J=8.7 Hz, 1H), 2.71 (s, 6H); MS (ESI) m/z: 415.0 (M+H⁺), 437.0 (M+Na⁺).

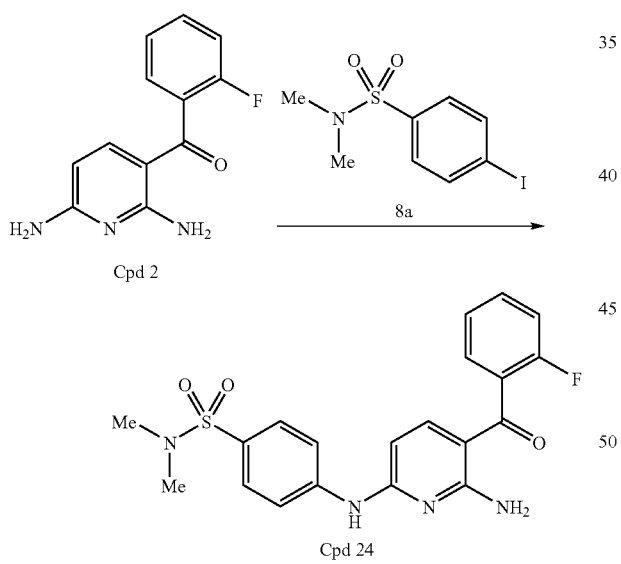

EXAMPLE 9

4-[(6-amino-5-benzoyl-2-pyridinyl)amino]-N,N-dimethylbenzenesulfonamide (Compound 25)

Compound 25 was prepared by the nucleophilic substitution of Compound 3 with N,N-dimethyl-4-iodobenzenesulfonamide Compound 8a (80% yield). ¹H NMR (300 MHz, CDCl₃) δ 7.65 (m, 10H), 2.74 (m, 6H); MS (ESI) n/z: 397.1 (M+H⁺).

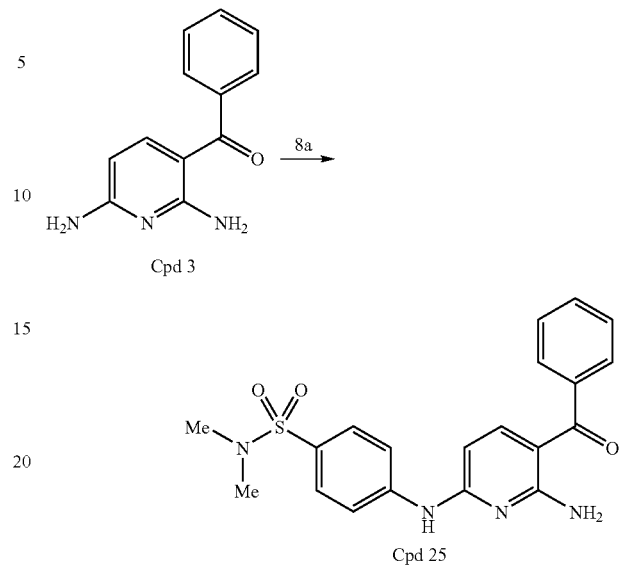

Using the procedure of Example 9, other compounds of the present invention were prepared:

| Cpd | Name | Materials |
|---|---|---|
| 26 | 4-[(6-amino-5-benzoyl-2-pyridinyl)amino]-N,N-diethylbenzenesulfonamide (33% yield)¹H NMR(300 MHz, CDCl₃) δ 7.70(m, 5H), 7.49(m, 6H), 3.23(q, J=7.2Hz, 4H), 1.15(t, J=7.2Hz, 6H); MS(ESI)m/z: 425.0(M+H⁺) | Use N,N-diethyl-4-iodobenzene-sulfonamide in place of Compound 8a |

EXAMPLE 10

4-[[6-amino-5-(2-furanylcarbonyl)-2-pyridinyl]amino]-N,N-dimethyl benzenesulfonamide (Compound 27)

Compound 27 was prepared by the nucleophilic substitution of Compound 4 with N,N-dimethyl-4-iodobenzenesulfonamide (Compound 8a) (60% yield). ¹H NMR (300 MHz, CDCl₃) δ 8.38 (d, J=8.7 Hz, 1H), 7.86 (d, J=8.7 Hz, 1H), 7.68 (m, 6H), 7.16 (dd, J=0.5, 3.5 Hz, 1H), 7.12 (s, 1H), 6.56 (m, 1H), 6.18 (d, J=8.8 Hz, 1H), 2.71(s, 1H); MS (ESI) m/z: 387.1 (M+H⁺).

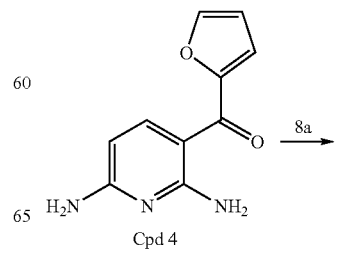

-continued

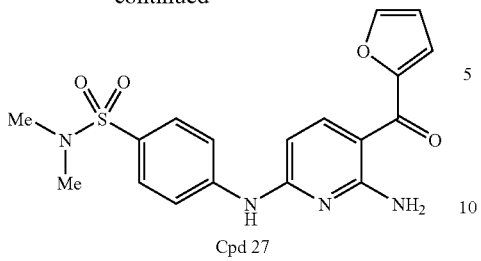

Cpd 27

Using the procedure of Example 10, other compounds of the present invention were prepared:

| Cpd | Name | Materials |
|---|---|---|
| 28 | 4-[[6-amino-5-(2-furanylcarbonyl)-2-pyridinyl]amino]-N,N-diethylbenzenesulfonamide (27% yield) $^1$H NMR(300 MHz, CDCl$_3$) δ 8.37(d, J=8.7Hz, 1H), 7.76(d, J=8.9Hz, 2H), 7.66(d, J=8.8Hz, 2H), 7.16(m, 1H), 6.98(s, 1H), 6.57(m, 1H), 6.18(d, J=8.7Hz, 1H), 3.24(q, 4H), 1.15(t, 6H); MS(ESI)m/z: 415.0 (M+H$^+$), 438.1(M+Na$^+$) | Use N,N-diethyl-4-iodobenzene-sulfonamide in place of Compound 8a |

EXAMPLE 11

4-[[6-amino-5-(2-thienylcarbonyl)-2-pyridinyl]amino]-N,N-dimethylbenzene sulfonamide (Compound 29)

Compound 29 was prepared by the nucleophilic substitution of Compound 5 with N,N-dimethyl-4-iodobenzenesulfonamide (48% yield).

$^1$H NMR (300 MHz, CDCl$_3$) δ 8.06 (d, J=8.6 Hz, 1H), 7.73 (s, 4H), 6.51 (dd, J=1.1, 3.8 Hz, 1H), 7.13 (dd, J=1.3, 5.0 Hz, 1H), 7.04 (s, 1H), 2.71 (s, 6H); MS (ESI) m/z: 403.0 (M+H$^+$).

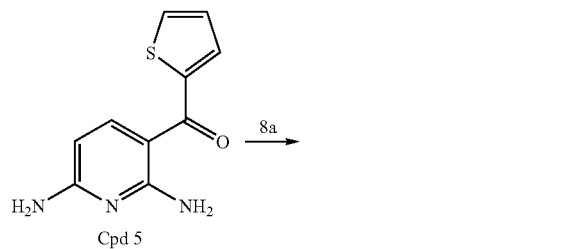

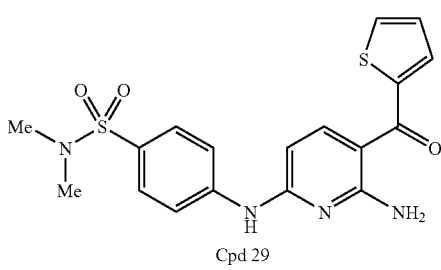

Cpd 29

EXAMPLE 12

(2,6-Diamino-4-butoxy-pyridin-3-yl)-(2,6-difluoro-phenyl)-methanone (Compound 31)

1-[6-Amino-4-butoxy-5-(2,6-difluoro-benzoyl)-pyridin-2-yl]-3-phenyl-urea (Compound 32)

1-[6-Amino-4-butoxy-5-(2,6-difluoro-benzoyl)-pyridin-2-yl]-3-phenyl-thiourea (Compound 33)

N-[6-Amino-4-butoxy-5-(2,6-difluoro-benzoyl)-pyridin-2-yl]-benzamide (Compound 34)

4-[6-Amino-4-butoxy-5-(2,6-difluoro-benzoyl)-pyridin-2-ylamino]-N,N-dimethyl-benzenesulfonamide (Compound 35)

4-[6-Amino-4-butoxy-5-(2,6-difluoro-benzoyl)-pyridin-2-ylamino]-benzenesulfonamide (Compound 36)

Chelidamic acid Compound 13a (4 g, 19.9 mmol) and n-BuI (iodobutane) (28 mL, 246 mmol) were dissolved in DMF (200 mL). K$_2$CO$_3$ (potassium carbonate) (27.4 g, 200 mmol) was added and the suspension was stirred at 100° C. for 48 hours. The solution was then concentrated in vacuo and the residue dissolved in ethyl acetate (400 mL) and water (100 mL). The aqueous layer was separated from the organic layer and was further extracted using ethyl acetate (200 mL×2). The combined organic layers were washed with a saturated sodium bicarbonate solution, then dried and concentrated. The crude product was purified by flash column chromatography to give an intermediate Compound 13b (1 g, 14% yield) as a colorless liquid. $^1$H NMR (300 MHz, CDCl$_3$) δ 7.75 (s, 2H), 4.40 (t, J=6.9 Hz, 4H), 4.13 (t, 2H), 1.82 (m, 6H), 1.50 (m, 6H), 0.99 (m, 9H); MS (ESI) m/z: 352 (M+H$^+$).

Compound 13b (1 g, 2.85 mmol) was dissolved in 95% ethanol (50 mL) and excess hydrazine hydrate (5 mL) was added to the solution. The reaction mixture was heated to reflux for three hours, then cooled to room temperature to induce precipitation. The solid was filtrated, washed with ethanol and dried to afford an intermediate Compound 13c (0.56 g, 73% yield) as white needles. $^1$H NMR (300 MHz, DMSO) δ 10.60(s, 2H), 7.57 (s, 2H), 4.19 (t, 2H), 1.737 (m, 2H), 1.45 (m, 2H), 0.94 (t, 3H); MS (ESI) m/z: 268 (M+H$^+$), 290 (M+Na$^+$).

Compound 13c (1 g, 3.74 mmol) was suspended in 9% hydrochloric acid (24 mL). The suspension was cooled to 0° C. and a solution of sodium nitrate (0.9 g, 13 mmol) in water (9 mL) was added dropwise over a period of 40 minutes. The reaction was kept at 0° C. for another 15 minutes. The waxy precipitate was carefully filtrated, washed with H$_2$O and dried under the vacuum. The obtained solid was suspended in dry t-butanol (25 mL) and was refluxed for five hours. The result solution was concentrated and purified by column chromatography to afford intermediate Compound 13d (0.3 g, 21%) as white crystals. $^1$H NMR (300 MHz, CDCl$_3$) δ 7.19(s, 2H), 4.06 (t, 2H), 1.75 (m, 2H), 1.53 (m, 20H), 0.97 (m, 3H); MS (ESI) m/z: 382 (M+H$^+$), 404 (M+Na$^+$).

Compound 13d (0.82 g, 2.15 mmol) was dissolved in dry THF (15 mL) and tert-butyllithium (1.7M in pentane, 4.5 mL, 7.65 mmol) at −78° C. was added dropwise. The solution was stirred at −78° C. for 0.5 hours, then the temperature was raised to −20° C. and maintained for 2.5 hours. 2,6-Difluorobenzoyl chloride Compound 1a (0.3 mL, 2.37 mmol) was added quickly to the solution, then the reaction mixture was warmed to room temperature and stirred overnight. The reaction was quenched using icy water and extracted using ethyl acetate (3×50 mL). The combined organic layers were dried, concentrated and purified by column chromatography to afford intermediate Compound 13e (0.15 g, 37% yield based on recovered starting materials) as a yellow powder. $^1$H NMR (300 MHz, CDCl$_3$) δ 11.15(s, 1H), 7.88 (s, 1H), 7.28 (m, 1H), 7.23 (s, 1H), 6.91 (dd, 2H), 3.88 (t, 2H), 1.81 (m, 2H), 1.51 (d, 18H), 1.24~0.79 (m, 5H); MS (ESI) m/z: 522 (M+H$^+$), 544 (M+Na$^+$).

Compound 13e (92 mg, 0.18 mmol) was dissolved in a (1:1) trifluoroacetic acid:dichloromethane solution (2 mL). The mixture was stirred at room temperature for 5 hours then concentrated under vacuum. The residue was neutralized using a saturated sodium bicarbonate solution (5 mL) and extracted with ethyl acetate (20 mL×3). The combined organic layers were dried, concentrated and purified by column chromatography to afford Compound 31 (48 mg, 86%) as a yellow powder. $^1$H NMR (300 MHz, CD$_3$COCD$_3$) δ 7.42 (m, 1H), 7.02 (t, 2H), 5.53 (s, 1H), 3.73 (t, 2H), 1.35~0.76 (m, 9H); MS (ESI) m/z: 322 (M+H$^+$), 344 (M+Na$^+$).

Phenyl isocyanate Compound 13f (5 uL, 0.05 mmol) and then dropwise a K—O-t-Bu (potassium tert-butoxide) solution (1.0 M in THF, 40 uL, 0.04 mmol) were added to a solution of Compound 31 (12 mg, 0.04 mmol) in dry DMF (0.1 mL). The mixture was stirred for 5 minutes and the reaction was quenched with the addition of water. The solution was diluted with ethyl acetate (50 mL) and the organic layer was washed with water, then dried and concentrated to give Compound 32 (7 mg, 43% yield) as a yellow solid. $^1$H NMR (300 MHz, CD$_3$COCD$_3$) δ 11.45 (s, br, 1H), 8.76 (s, 1H), 7.7 (d, 2H), 7.46 (m, 1H), 7.31 (dd, 2H) 7.04 (m, 3H), 6.13 (s, 1H), 3.84 (t, 2H), 1.38~0.76 (m, 9H); MS (ESI) m/z: 441 (M+H$^+$), 463 (M+Na$^+$).

Phenyl thioisocyanate Compound 13g (5 uL, 0.05 mmol) and then dropwise a K—O-t-Bu solution (1.0 M in THF, 40 uL, 0.04 mmol) were added to Compound 31 (12 mg, 0.04 mmol) in a dry DMF solution (0.1 mL). The mixture was stirred for 20 minutes and the reaction was quenched with the addition of water. The solution was diluted with ethyl acetate (50 mL) and the organic layer was washed with water, then dried and concentrated to give Compound 33 (8 mg, 47% yield) as a yellow solid. $^1$H NMR (300 MHz, CDCl$_3$) δ 13.45 (s, br, 1H), 8.50 (s, 1H), 7.67 (d, 2H), 7.43 (m, 1H), 7.28 (dd, 2H) 6.92 (m, 3H), 5.59 (s, 1H), 3.73 (t, 2H), 1.26~0.74 (m, 9H); MS (ESI) m/z: 457 (M+H$^+$), 479 (M+Na$^+$).

Compound 31 (12 mg, 0.04 mmol), DMAP (4-N,N-dimethylaminopyridine) (5.7 mg, 0.05 mmol) and triethylamine (10 uL, 0.07 mmol) were dissolved in anhydrous THF (0.1 mL) then a freshly prepared solution of benzoyl chloride Compound 13h (1 M in DCM, 50 uL) was added dropwise. The reaction mixture was stirred at room temperature overnight then diluted with ethyl acetate and washed with 1N hydrochloric acid. The organic layer was dried and purified by column chromatography to yield Compound 34 (1 mg, 5% yield) as a yellow solid. $^1$H NMR (300 MHz, CD$_3$COCD$_3$) δ 13.45 (s, br, 1H), 8.50 (s, 1H), 7.67 (d, 2H), 7.43 (m, 1H), 7.28 (dd, 2H) 6.92 (m, 3H), 5.59 (s, 1H), 3.73 (t, 2H), 1.26~0.74 (m, 9H); MS (ESI) m/z: 457 (M+H$^+$), 479 (M+Na$^+$).

N,N-Dimethyl-4-iodobenzenesulfonamide Compound 8a (18 mg, 0.057 mmol), Compound 31 (15 mg, 0.047 mmol), Pd$_2$(dba)$_3$ (3 mg, 0.003 mmol), BINAP (3 mg, 0.005 mmol) and cesium carbonate (18 mg, 0.055 mmol) in dry dioxane (0.5 mL) were stirred at 105° C. overnight. The mixture was then cooled to room temperature and diluted with water (5 mL) and ethyl acetate (40 mL). The organic layer was separated, dried, concentrated and purified by column chromatography to yield Compound 35 (7 mg, 30% yield) as a yellow powder. $^1$H NMR (300 MHz, CD$_3$COCD$_3$) δ 8.15 (d, 2H), 7.69 (d, 2H), 7.45 (m, 1H), 7.05 (m, 2H), 5.80 (s, 1H), 3.78 (t, 2H), 2.80 (s, 3H), 2.72 (s, 3H), 1.32–0.76 (m, 7H); MS (ESI) m/z: 505 (M+H$^+$), 527 (M+Na$^+$).

N-(t-Butyloxycarbonyl)-4-iodobenzenesulfonamide Compound 13i (prepared as described in Silvia C., et al, *Eur. J. Org. Chem.*, 2001, 329–337) (22 mg, 0.056 mmol), Compound 31 (15 mg, 0.047 mmol), Pd$_2$(dba)$_3$ (3 mg, 0.003 mmol), BINAP (3 mg, 0.005 mmol) and cesium carbonate (18 mg, 0.055 mmol) in dry dioxane (0.5 mL) were stirred at 105° C. overnight. The mixture was then cooled to room temperature and diluted with water (5 mL) and ethyl acetate (40 mL). The organic layer was separated, dried, concentrated and purified by column chromatography to yield Compound 13j (8 mg, 30% yield) as a yellow powder. $^1$H NMR (300 MHz, CD$_3$COCD$_3$) δ 8.99 (s, 1H), 8.11 (d, 2H), 7.91 (d, 2H), 7.44 (m, 1H), 7.01 (m, 2H), 5.80 (s, 1H), 3.77 (t, 2H), 1.36 (s, 9H), 1.31–0.75 (m, 7H); MS (ESI) m/z: 577 (M+H$^+$), 599 (M+Na$^+$).

Compound 13j (8 mg, 0.002 mmol) was dissolved in a (1:1) trifluoroacetic acid:dichloromethane solution (2 mL) and stirred at room temperature for 3 hours. The solution was concentrated and treated with ethyl acetate (40 mL) and saturated sodium bicarbonate solution (5 mL). The organic layer was dried, concentrated and purified by column chromatography to afford Compound 36 (5 mg, 76% yield) as a yellow solid. $^1$H NMR (300 MHz, CD$_3$COCD$_3$) δ 8.01 (d, 2H), 7.77 (d, 2H), 7.44 (m, 1H), 7.01 (m, 2H), 5.77 (s, 1H), 3.78 (t, 2H), 1.30–0.76 (m, 7H); MS (ESI) m/z: 477 (M+H$^+$) 499 (M+Na$^+$).

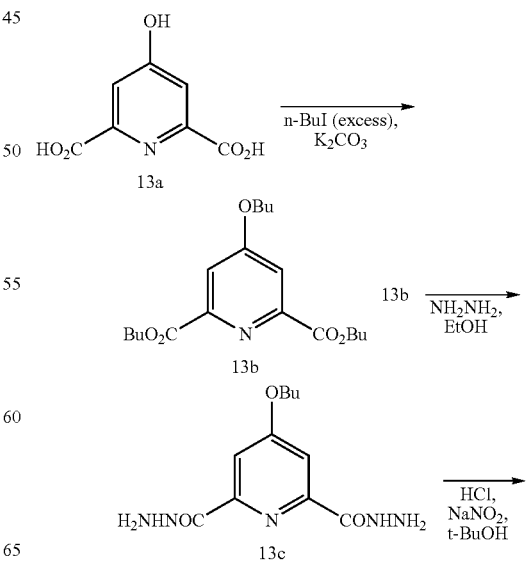

-continued

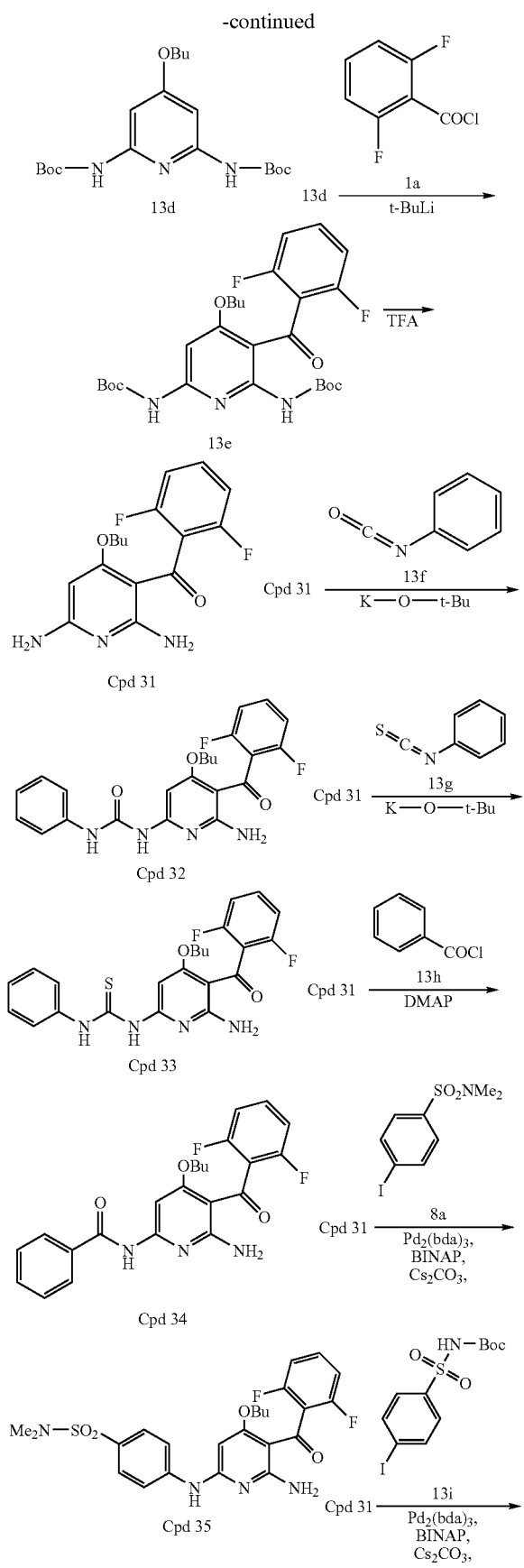

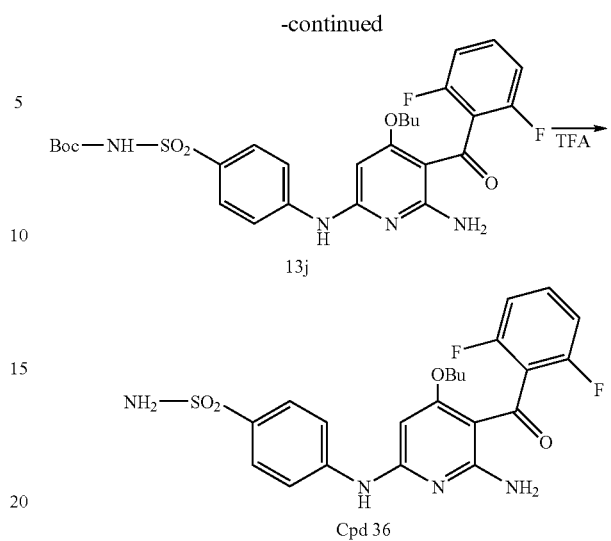

BIOLOGICAL EXAMPLES

The utility of the compounds to treat or ameliorate a cyclin dependent kinase mediated disorder was determined using the following procedures.

EXAMPLE 1

CDK1 Screening Assay

A kinase reaction mixture was prepared containing 50 mM Tris-HCl pH=8, 10 mM $MgCl_2$, 0.1 mM $Na_3PO_4$, 1 mM DTT, 10 μM ATP, 0.025 μM biotinylated histone-H1 peptide substrate and 0.2 μCuries per well $^{33P}$-γ-ATP [2000–3000 Ci/mmol]. 70 μL of the kinase reaction mixture was dispensed into the well of a streptavidin coated FlashPlate™ (Cat. #SMP103, NEN, Boston, Mass.). Then 1 μL of test compound stock in 100% DMSO was added to the wells resulting in a final concentration of 1% DMSO in the reaction with a 100 μL final reaction volume. CDK1:Cyclin-B protein[1] was diluted in 50 mM Tris-HCl pH=8.0, 0.1% BSA at a concentration of 1 ng per microliter. 30 μL (30 ng enzyme per test well) was added to each well to initiate the reaction, The reaction was incubated for one hour at 30° C. At the end of the 1-hour incubation, the reaction was terminated by aspirating the reaction mixture from the plate and washing the wells twice with PBS containing 100 mM EDTA. The histone-H1 biotinylated peptide substrate became immobilized on the Flashplate™ and the incorporation of $^{33}$P-γ-ATP was measured by reading the plate on a scintillation counter. Inhibition of the enzymatic activity of CDK1 was measured by observing a reduced amount of $^{33}$P-γ-ATP incorporated into the immobilized peptide.

[1]CDK1 (cyclin dependent kinase 1) was isolated from insect cells expressing both the human CDK1 catalytic subunit and its positive regulatory subunit Cyclin B (CDK1: New England Biolabs, Beverly, Mass., Cat. #6020); Cyclin-B: BIOMOL, Plymouth Meeting, Pa., Cat. #SE-195); Peptide Substrate (Biotin)KTPKKAKKPKTPKKAKKL-Amide.

$IC_{50}$ data for CDK1 is shown in Table 1. Using this method, compounds of the present invention were demonstrated to be effective as inhibitors of CDK1 with $IC_{50}$ values ranging from 0.26 to >100 μM. $IC_{50}$ values listed as >10 or >100 indicate no observed 50% inhibition at the highest dose tested, nor was an inhibition maximum observed.

TABLE 1

| Cpd | CDK1 IC$_{50}$ (μM) |
|---|---|
| 1 | 2.6 |
| 2 | 8.23 |
| 2b | >10 |
| 3 | 1.09 |
| 4 | >100 |
| 5 | >100 |
| 6 | 0.36 |
| 7 | 0.26 |
| 8 | 1.37 |
| 9 | 0.96 |
| 10 | 2.67 |
| 11 | 6.16 |
| 12 | >10 |
| 13 | 21.7 |
| 14 | 12.3 |
| 15 | 0.95 |
| 16 | 10 |
| 17 | 0.75 |
| 18 | 1.14 |
| 19 | 0.74 |
| 20 | 11.6 |
| 21 | >100 |
| 22 | >100 |
| 23 | >100 |
| 24 | 1.96 |
| 25 | 2.19 |
| 26 | >100 |
| 27 | 10.7 |
| 28 | >100 |
| 29 | 12.7 |
| 31 | 1.16 |
| 32 | >100 |
| 33 | >100 |
| 34 | >100 |
| 35 | ~1 |
| 36 | 0.28 |

EXAMPLE 2

CDK2 Screening Assay

Using the procedure and materials of Example 1, replacing CDK1:Cyclin-B protein with CDK2:Cyclin-E protein[2], the IC$_{50}$ data for CDK2 is shown in Table 2.

[2] CDK2 (cyclin dependent kinase 2) in complex with cyclin E is commercially available (Upstate Biotechnology, Lake Placid, N.Y.); Peptide Substrate (Biotin)KTPKKAKKPKTPKKAKKL-Amide IC$_{50}$ data for CDK2 is shown in Table 2. Using this method, compounds of the present invention were demonstrated to be effective as inhibitors of CDK2 with IC$_{50}$ values ranging from 0.07 to ~100 μM. IC$_{50}$ values listed as ~100 indicate no observed 50% inhibition at the highest dose tested, nor was an inhibition maximum observed.

TABLE 2

| Cpd | CDK2 IC$_{50}$ (μM) |
|---|---|
| 31 | 1.32 |
| 32 | ~100 |
| 33 | ~100 |
| 34 | ~100 |
| 35 | 0.62 |
| 36 | 0.07 |

EXAMPLE 3

VEGF-R2 Kinase Screening Assay

A kinase reaction mixture was prepared containing 50 mM Tris-HCl pH=8, 10 mM MgCl$_2$, 0.1 mM Na$_3$PO$_4$, 1 mM DTT, 10 μM ATP, 0.025 uM biotinylated peptide substrate and 0.8 μCuries per well $^{33P}$-γ-ATP [2000–3000 Ci/mmol]. 70 μL of the kinase reaction mixture was dispensed into the well of a streptavidin coated FlashPlate™ (Cat. #SMP103, NEN, Boston, Mass.). 1 μL of test compound stock in 100% DMSO was added to the wells resulting in a final concentration of 1% DMSO in the mixture with a 100 μL final reaction volume. Soluble rat VEGF-R2 kinase[3] was diluted in 50 mM Tris-HCl pH=8.0, 0.1% BSA at a concentration of 5 ng per microliter and 30 μL (150 ng enzyme per test well) was added to each well to initiate the reaction. The reaction was incubated for one hour at 30° C. At the end of the 1-hour incubation, the reaction was terminated by aspirating the reaction mixture from the plate and washing the wells twice with PBS containing 100 mM EDTA. The PLC1 biotinylated peptide substrate became immobilized on the Flashplate™ and the incoporation of $^{33}$P-γ-ATP was measured by reading the plate on a scintillation counter. Inhibition of the enzymatic activity of the VEGF-R was measured by observing a reduced amount of $^{33}$P-γ-ATP incorporated into the immobilized peptide.

[3] VEGF-R2 kinase (Vascular Endothelial Growth Factor Receptor-2): a fusion protein containing a polyhistidine tag at the N-terminus followed by amino acids 786–1343 of the rat VEGF-R2 kinase domain GenBank Accession #U93306); Peptide Substrate (Biotin)KHKKLAEGSAYEEV-Amide IC$_{50}$ data for VEGF-R2 kinase is shown in Table 3. Using this method, compounds of the present invention were demonstrated to be effective as inhibitors of VEGF-R2 kinase with IC$_{50}$ values ranging from 40.24 to >100 μM. IC$_{50}$ values listed as >10 or >100 indicate no observed 50% inhibition at the highest dose tested, nor was an inhibition maximum observed.

TABLE 3

| Cpd | VEGF-R IC$_{50}$ (μM) |
|---|---|
| 1 | >10 |
| 2 | >10 |
| 2b | >10 |
| 3 | >10 |
| 4 | >100 |
| 5 | >100 |
| 6 | >10 |
| 7 | >10 |
| 8 | >10 |
| 9 | >10 |
| 10 | >100 |
| 11 | >100 |
| 12 | >10 |
| 13 | >100 |
| 14 | >100 |
| 15 | >10 |
| 16 | >10 |
| 17 | >10 |
| 18 | >10 |
| 19 | >10 |
| 20 | >100 |
| 21 | >100 |
| 22 | >100 |
| 23 | >100 |
| 24 | >100 |
| 25 | >100 |
| 26 | >100 |
| 27 | >100 |
| 28 | >100 |

TABLE 3-continued

VEGF-R

| Cpd | IC$_{50}$ (µM) |
|---|---|
| 29 | >100 |
| 31 | 40.24 |
| 32 | >100 |
| 33 | >100 |
| 34 | >100 |
| 35 | >100 |
| 36 | >100 |

EXAMPLE 4

HER-2 Kinase Screening Assay

Using the procedure and materials of Example 3, replacing VEGF-R2 kinase with HER2[4], the IC$_{50}$ data for HER2 kinase is shown in Table 4.

[4]HER2 (Human Epidermal Growth Factor Receptor-2): a construct containing a polyhistidine tag at the N-terminus followed by 24 additional non-native amino acids beginning at amino acid 676 (Accession number M11730) followed by the remainder of the HER2 cytoplasmic domain; Peptide Substrate (Biotin)KHKKLAEGSAYEEV-Amide.

Using this method, compounds of the present invention were demonstrated to be effective as inhibitors of HER-2 kinase with IC$_{50}$ values ranging from 1 to >100 µM. IC$_{50}$ values listed as >100 indicate no observed 50% inhibition at the highest dose tested, nor was an inhibition maximum observed.

TABLE 4

HER2

| Cpd | IC$_{50}$ (µM) |
|---|---|
| 31 | 1.14 |
| 32 | >100 |
| 33 | >100 |
| 34 | >100 |
| 35 | >100 |
| 36 | 1.0 |

EXAMPLE 5

Assay to Measure Inhibition of Cell Proliferation

The ability of a test compound to inhibit the proliferation of cell growth was determined by measuring incorporation of $^{14}$C-labelled thymidine into newly synthesized DNA within the cells. This method was used on cell lines derived from carcinomas originating from several tissues such as HeLa cervical adenocarcinoma (American Type Culture Collection (ATCC), Virginia, Cat. #CCL-2), HCT-116 colon carcinoma (CCL-247), MDA-MB-231 (Xenogen Corp.), PC-3 prostate adenocarcinoma (ATCC CRL-1435) and A375 malignant melanoma (ATCC CRL-1619).

Using this method, the effect of a compound on cell growth for cells with many different phenotypes can be determined. Cells were trypsinized and counted and 3000–8000 cells were added to each well of a 96-well CytoStar tissue culture treated scintillating microplate (Amersham #RPNQ0160) in complete medium in a volume of 100 µl. Cells were incubated for 24 hours in complete medium at 37° C. in an atmosphere containing 5% CO$_2$. 1 µL of test compound in 100% DMSO was then added to the wells of the plate. DMSO only was added to control wells. Cells were incubated for 24 more hours in complete medium at 37° C. in an atmosphere containing 5% CO$_2$. Methyl $^{14}$C-thymidine (56 mCi/mmol) (NEN #NEC568 or Amersham #CFA532) was diluted in complete medium and 0.2 µCi/well was added to each well of the CytoStar plate in a volume of 20 µL. The plate was incubated for 24 hours at 37° C. plus 5% CO$_2$ in drug plus $^{14}$C-thymidine. The contents of the plate were discarded into a $^{14}$C radioactive waste container by inverting the plate and the plate was washed twice with 200 µL PBS. 200 µL of PBS was then added to each well. The top of the plate was sealed with a transparent plate sealer and a white plate backing sealer (Packard #6005199) was applied to the bottom of the plate. The degree of methyl $^{14}$C-thymidine incorporation was quantified on a Packard Top Count.

The IC$_{50}$ data (in µM) for a compound tested in the model of Example 5 is shown in Table 5. Using this method, compounds of the present invention are demonstrated to be effective as inhibitors of cell proliferation with IC$_{50}$ values ranging from 2.96 to 10.7 µM.

TABLE 5

Inhibition of Cell Proliferation IC$_{50}$ (µM)

| Cell line | Cpd 36 |
|---|---|
| HeLa | 10.7 |
| HCT-116 | 6.78 |
| A375 | 2.96 |

While the foregoing specification teaches the principles of the present invention, with examples provided for the purpose of illustration, it will be understood that the practice of the invention encompasses all of the usual variations, adaptations and modifications as come within the scope of the following claims and their equivalents.

What is claimed is:

1. A compound of Formula (I):

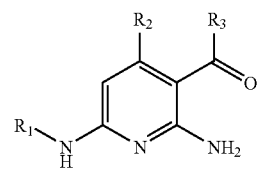

Formula (I)

wherein:
R$_1$ is selected from:
(1) hydrogen;
(2) aryl optionally substituted with
  (a) one or more substituents independently selected from C$_{1-8}$alkyl, C$_{1-8}$alkoxy, amino optionally mono or disubstituted with C$_{1-8}$alkyl, cyano, halogen, halogen-substituted C$_{1-8}$alkyl, halogen-substituted C$_{1-8}$alkoxy, hydroxy or nitro;
  (b) one —SO$_2$-amino substituent optionally mono or disubstituted on amino with C$_{1-8}$alkyl, C$_{1-8}$alkylamino optionally mono or disubstituted on amino with C$_{1-8}$alkyl, C$_{1-8}$alkyl-aryl, C(O)O-t-butyl or heteroaryl;
  (c) one —SO$_2$-heterocyclyl substituent;
  (d) one —NHSO$_2$-aryl substituent;
  (e) one —C(O)amino substituent optionally mono or disubstituted on amino with C$_{1-8}$alkyl;

(f) one —NHC(O)— substituent terminating with C$_{1-8}$alkyl or aryl;
(g) one —CO$_2$— substituent terminating with hydrogen or C$_{1-8}$alkyl;
(h) one —NHC(O)NH-aryl substituent; or,
(i) one —NHC(S)NH-aryl substituent;
(j) one substituent selected from heterocyclyl selected from piperidinyl, piperazinyl, morpholinyl, thiomorpholinyl, or tetra-hydro-pyridazinyl, aryl or heteroaryl selected from pyrrolyl, oxazolyl, thiazolyl, imidazolyl, pyrazolyl, isoxazolyl or isothiazolyl;
(3) heteroaryl optionally substituted with one or more substituents independently selected from C$_{1-8}$alkyl, C$_{1-8}$alkoxy, amino optionally mono or disubstituted with C$_{1-8}$alkyl, cyano, halogen, halogen-substituted C$_{1-8}$alkyl, halogen-substituted C$_{1-8}$alkoxy, hydroxy or nitro;
(4) —C(O)— terminating with aryl, heteroaryl or alkyl;
(5) —C(O)NH— substituent terminating with aryl, heteroaryl or alkyl; or,
(6) —C(S)NH— substituent terminating with aryl, heteroaryl or alkyl;

R$_2$ is selected from hydrogen, C$_{1-8}$alkoxy, amino optionally mono or disubstituted with C$_{1-8}$alkyl, cyano, halogen, hydroxy, mercapto, S(C$_{1-8}$)alkyl or nitro;

wherein C$_{1-8}$alkyl and C$_{1-8}$alkoxy, whether alone or as part of a substituent group are optionally substituted with one or more substituents independently selected from halogen or amino optionally mono or disubstituted on amino with C$_{1-8}$alkyl;

R$_3$ is selected from aryl or heteroaryl,
(1) wherein aryl is optionally substituted with one or more substituents independently selected from C$_{1-8}$alkyl, C$_{1-8}$alkoxy, amino optionally mono or disubstituted with C$_{1-8}$alkyl, cyano, halogen, halogen-substituted C$_{1-8}$alkyl, halogen-substituted C$_{1-8}$alkoxy, hydroxy or nitro; and
(2) wherein heteroaryl is optionally substituted on
(a) a ring carbon atom with one or more substituents selected from C$_{1-8}$alkyl, C$_{1-8}$alkoxy, amino optionally mono or disubstituted with C$_{1-8}$alkyl, cyano, halogen, halogen-substituted C$_{1-8}$alkyl, halogen-substituted C$_{1-8}$alkoxy, hydroxy or nitro; or on
(b) a ring nitrogen atom with one C$_{1-8}$alkyl substituent, or a pharmaceutically acceptable form thereof.

2. A compound of claim 1, wherein said compound is selected from the group consisting of compounds of Formula (Ia), wherein R$_2$ is hydrogen and R$_1$ and R$_3$ are dependently selected from:

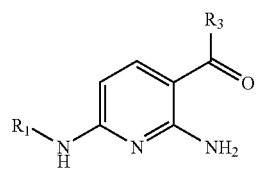

Formula (Ia)

| Cpd | R$_1$ | R$_3$ |
|---|---|---|
| 1 | H | (2,6-F$_2$)Ph |
| 2 | H | (2-F)Ph |
| 2b | [4-SO$_2$N(CH$_2$—Ph)$_2$]Ph | (2,6-F$_2$)Ph |
| 3 | H | Ph |
| 4 | H | fur-2-yl |

-continued

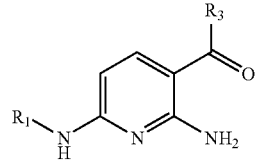

Formula (Ia)

| Cpd | R$_1$ | R$_3$ |
|---|---|---|
| 5 | H | thien-2-yl |
| 6 | (4-SO$_2$NH$_2$)Ph | (2,6-F$_2$)Ph |
| 7 | [4-SO$_2$N(CH$_3$)$_2$]Ph | (2,6-F$_2$)Ph |
| 8 | (4-CN)Ph | (2,6-F$_2$)Ph |
| 9 | (4-NO$_2$)Ph | (2,6-F$_2$)Ph |
| 10 | (3-NO$_2$)Ph | (2,6-F$_2$)Ph |
| 11 | (3-Cl)Ph | (2,6-F$_2$)Ph |
| 12 | (2-NO$_2$)Ph | (2,6-F$_2$)Ph |
| 13 | Ph | (2,6-F$_2$)Ph |
| 14 | pyridin-2-yl | (2,6-F$_2$)Ph |
| 15 | [4-C(O)NH$_2$]Ph | (2,6-F$_2$)Ph |
| 16 | (4-CO$_2$H)Ph | (2,6-F$_2$)Ph |
| 17 | (4-NH$_2$)Ph | (2,6-F$_2$)Ph |
| 18 | [4-NH(CH$_3$)]Ph | (2,6-F$_2$)Ph |
| 19 | [4-SO$_2$NH(Ph)]Ph | (2,6-F$_2$)Ph |
| 20 | [2-NH$_2$]Ph | (2,6-F$_2$)Ph |
| 21 | [2-NHC(O)CH$_3$]Ph | (2,6-F$_2$)Ph |
| 22 | [2-NHC(O)Ph]Ph | (2,6-F$_2$)Ph |
| 23 | (2-NHSO$_2$Ph)Ph | (2,6-F$_2$)Ph |
| 24 | [4-SO$_2$N(CH$_3$)$_2$]Ph | (2-F)Ph |
| 25 | [4-SO$_2$N(CH$_3$)$_2$]Ph | Ph |
| 26 | [4-SO$_2$N(CH$_2$CH$_3$)$_2$]Ph | Ph |
| 27 | [4-SO$_2$N(CH$_3$)$_2$]Ph | fur-2-yl |
| 28 | [4-SO$_2$N(CH$_2$CH$_3$)$_2$]Ph | fur-2-yl, and |
| 29 | [4-SO$_2$N(CH$_3$)$_2$]Ph | thien-2-yl. |

3. A compound of claim 1, wherein said compound is selected from the group consisting of compounds of Formula (Ib), wherein R$_2$ is n-butoxy, R$_3$ is (2,6-F$_2$)Ph and R$_1$ is selected from:

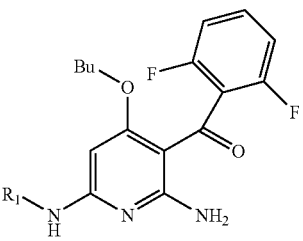

Formula (Ib)

| Cpd | R$_1$ |
|---|---|
| 31 | H |
| 32 | C(O)NH(Ph) |
| 33 | C(S)NH(Ph) |
| 34 | C(O)Ph |
| 35 | [4-SO$_2$N(CH$_3$)$_2$]Ph |
| 36 | (4-SO$_2$NH$_2$)Ph. |

4. A pharmaceutical composition, comprising:
a compound of Formula (I)

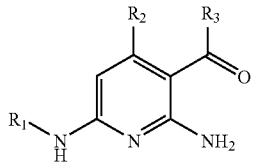

Formula (I)

wherein:
$R_1$ is selected from:
(1) hydrogen;
(2) aryl optionally substituted with
  (a) one or more substituents independently selected from $C_{1-8}$alkyl, $C_{1-8}$alkoxy, amino optionally mono or disubstituted with $C_{1-8}$alkyl, cyano, halogen, halogen-substituted $C_{1-8}$alkyl, halogen-substituted $C_{1-8}$alkoxy, hydroxy or intro;
  (b) one —$SO_2$-amino substituent optionally mono or disubstituted on amino with $C_{1-8}$alkyl, $C_{1-8}$alkylamino optionally mono or disubstituted on amino with $C_{1-8}$alkyl, $C_{1-8}$alkyl-aryl, C(O)O-t-butyl or heteroaryl;
  (c) one —$SO_2$-heterocyclyl substituent;
  (d) one —$NHSO_2$-aryl substituent;
  (e) one —C(O)amino substituent optionally mono or disubstituted on amino with $C_{1-8}$alkyl;
  (f) one —NHC(O)— substituent terminating with $C_{1-8}$alkyl or aryl;
  (g) one —$CO_2$— substituent terminating with hydrogen or $C_{1-8}$alkyl;
  (h) one —NHC(O)NH-aryl substituent; or,
  (i) one —NHC(S)NH-aryl substituent;
  (j) one substituent selected from heterocyclyl selected from piperidinyl, piperazinyl, morpholinyl, thiomorpholinyl, or tetra-hydro-pyridazinyl, aryl or heteroaryl selected from pyrrolyl, oxazolyl, thiazolyl, imidazolyl, pyrazolyl, isoxazolyl or isothiazolyl;
(3) heteroaryl optionally substituted with one or more substituents independently selected from $C_{1-8}$alkyl, $C_{1-8}$alkoxy, amino optionally mono or disubstituted with $C_{1-8}$alkyl, cyano, halogen, halogen-substituted $C_{1-8}$alkyl, halogen-substituted $C_{1-8}$alkoxy, hydroxy or nitro;
(4) —C(O)— terminating with aryl, heteroaryl or alkyl;
(5) —C(O)NH— substituent terminating with aryl, heteroaryl or alkyl; or,
(6) —C(S)NH— substituent terminating with aryl, heteroaryl or alkyl;
$R_2$ is selected from hydrogen, $C_{1-8}$alkoxy, amino optionally mono or disubstituted with $C_{1-8}$alkyl, cyano, halogen, hydroxy, mercapto, S($C_{1-8}$)alkyl or nitro;
wherein $C_{1-8}$alkyl and $C_{1-8}$alkoxy, whether alone or as part of a substituent group are optionally substituted with one or more substituents independently selected from halogen or amino optionally mono or disubstituted on amino with $C_{1-8}$alkyl;
$R_3$ is selected from aryl or heteroaryl,
  (1) wherein aryl is optionally substituted with one or more substituents independently selected from $C_{1-8}$alkyl, $C_{1-8}$alkoxy, amino optionally mono or disubstituted with $C_{1-8}$alkyl, cyano, halogen, halogen-substituted $C_{1-8}$alkyl, halogen-substituted $C_{1-8}$alkoxy, hydroxy or nitro; and
  (2) wherein heteroaryl is optionally substituted on
    (a) a ring carbon atom with one or more substituents selected from $C_{1-8}$alkyl, $C_{1-8}$alkoxy, amino optionally mono or disubstituted with $C_{1-8}$alkyl, cyano, halogen, halogen-substituted $C_{1-8}$alkyl, halogen-substituted $C_{1-8}$alkoxy, hydroxy or nitro; or on
    (b) a ring nitrogen atom with one $C_{1-8}$alkyl substituent,
or a pharmaceutically acceptable form thereof,
and one or more pharmaceutically-acceptable excipients.

5. The composition of claim 4, wherein the composition is sterile.

6. The composition of claim 4, wherein the composition has an inhibition constant against a CDK enzyme, wherein the CDK enzyme is selected from the group consisting of CDK 1 and CDK 2 and wherein the inhibition constant is selected from the group consisting of about 25 μM or less; about 10 μM or less; about 1 μM or less; and about 0.5 μM or less.

7. The composition of claim 4, wherein said compound is present in an amount between about 0.01 and about 500 milligrams.

8. The composition of claim 4, suitable for administration by a route selected from the group consisting of subcutaneous, intravenous, intramuscular, intraperitoneal, buccal, ocular, rectal, parenteral, intrasystemic, intravaginal, topical, oral, nasal and transdermal.

9. A method of inhibiting a CDK enzyme selected from the group consisting of CDK 1 and CDK 2, comprising contacting the CDK enzyme with one or more compounds of Formula (I)

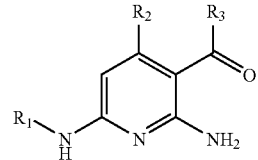

Formula (I)

wherein:
$R_1$ is selected from:
(1) hydrogen;
(2) aryl optionally substituted with
  (a) one or more substituents independently selected from $C_{1-8}$alkyl, $C_{1-8}$alkoxy, amino optionally mono or disubstituted with $C_{1-8}$alkyl, cyano, halogen, halogen-substituted $C_{1-8}$alkyl, halogen-substituted $C_{1-8}$alkoxy, hydroxy or nitro;
  (b) one —$SO_2$-amino substituent optionally mono or disubstituted on amino with $C_{1-8}$alkyl, $C_{1-8}$alkylamino optionally mono or disubstituted on amino with $C_{1-8}$alkyl, $C_{1-8}$alkyl-aryl, C(O)O-t-butyl or heteroaryl;
  (c) one —$SO_2$-heterocyclyl substituent;
  (d) one —$NHSO_2$-aryl substituent;
  (e) one —C(O)amino substituent optionally mono or disubstituted on amino with $C_{1-8}$alkyl;
  (f) one —NHC(O)— substituent terminating with $C_{1-8}$alkyl or aryl;
  (g) one —$CO_2$— substituent terminating with hydrogen or $C_{1-8}$alkyl;
  (h) one —NHC(O)NH-aryl substituent; or, (i) one —NHC(S)NH-aryl substituent;

(j) one substituent selected from heterocyclyl selected from piperidinyl, piperazinyl, morpholinyl, thiomorpholinyl, or tetra-hydro-pyridazinyl, aryl or heteroaryl selected from pyrrolyl, oxazolyl, thiazolyl, imidazolyl, pyrazolyl, isoxazolyl or isothiazolyl;

(3) heteroaryl optionally substituted with one or more substituents independently selected from $C_{1-8}$alkyl, $C_{1-8}$alkoxy, amino optionally mono or disubstituted with $C_{1-8}$alkyl, cyano, halogen, halogen-substituted $C_{1-8}$alkyl, halogen-substituted $C_{1-8}$alkoxy, hydroxy or nitro;

(4) —C(O)— terminating with aryl, heteroaryl or alkyl;

(5) —C(O)NH— substituent terminating with aryl, heteroaryl or alkyl; or, (6) —C(S)NH— substituent terminating with aryl, heteroaryl or alkyl;

$R_2$ is selected from hydrogen, $C_{1-8}$alkoxy, amino optionally mono or disubstituted with $C_{1-8}$alkyl, cyano, halogen, hydroxy, mercapto, $S(C_{1-8})$alkyl or nitro;

wherein $C_{1-8}$alkyl and $C_{1-8}$alkoxy, whether alone or as part of a substituent group are optionally substituted with one or more substituents independently selected from halogen or amino optionally mono or disubstituted on amino with $C_{1-8}$alkyl;

$R_3$ is selected from aryl or heteroaryl, (1) wherein aryl is optionally substituted with one or more substituents independently selected from $C_{1-8}$alkyl, $C_{1-8}$alkoxy, amino optionally mono or disubstituted with $C_{1-8}$alkyl, cyano, halogen, halogen-substituted $C_{1-8}$alkyl, halogen-substituted $C_{1-8}$alkoxy, hydroxy or nitro; and (2) wherein heteroaryl is optionally substituted on
  (a) a ring carbon atom with one or more substituents selected from $C_{1-8}$alkyl, $C_{1-8}$alkoxy, amino optionally mono or disubstituted with $C_{1-8}$alkyl, cyano, halogen, halogen-substituted $C_{1-8}$alkyl, halogen-substituted $C_{1-8}$alkoxy, hydroxy or nitro; or on
  (b) a ring nitrogen atom with one $C_{1-8}$alkyl substituent, or a pharmaceutically acceptable form thereof.

10. A method of treating a CDK 1 or CDK 2 mediated disorder, wherein the disorder is selected from the group consisting of cervical adenocarcinoma, colon carcinoma and malignant melanoma, comprising administering a therapeutically effective amount of a compound of claim 1 to a subject in need thereof.

* * * * *